(12) United States Patent
Sato et al.

(10) Patent No.: US 10,303,055 B2
(45) Date of Patent: *May 28, 2019

(54) RESIST COMPOSITION AND METHOD FOR FORMING RESIST PATTERN

(71) Applicant: Mitsubishi Gas Chemical Company, Inc., Tokyo (JP)

(72) Inventors: Takashi Sato, Kanagawa (JP); Masatoshi Echigo, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/125,463

(22) PCT Filed: Mar. 13, 2015

(86) PCT No.: PCT/JP2015/057470
§ 371 (c)(1),
(2) Date: Sep. 12, 2016

(87) PCT Pub. No.: WO2015/137485
PCT Pub. Date: Sep. 17, 2015

(65) Prior Publication Data
US 2017/0075220 A1 Mar. 16, 2017

(30) Foreign Application Priority Data

Mar. 13, 2014 (JP) ................................. 2014-050767

(51) Int. Cl.
| | |
|---|---|
| G03F 7/16 | (2006.01) |
| G03F 7/20 | (2006.01) |
| G03F 7/32 | (2006.01) |
| G03F 7/40 | (2006.01) |
| G03F 7/004 | (2006.01) |
| G03F 7/038 | (2006.01) |
| C07C 39/15 | (2006.01) |

(52) U.S. Cl.
CPC ............ *G03F 7/0382* (2013.01); *C07C 39/15* (2013.01); *G03F 7/0045* (2013.01); *G03F 7/162* (2013.01); *G03F 7/168* (2013.01); *G03F 7/2037* (2013.01); *G03F 7/327* (2013.01); *G03F 7/40* (2013.01)

(58) Field of Classification Search
None
See application file for complete search history.

(56) References Cited

U.S. PATENT DOCUMENTS

| | | | |
|---|---|---|---|
| 3,702,245 | A | 11/1972 | Simon et al. |
| 4,115,128 | A | 9/1978 | Kita |
| 4,670,495 | A | 6/1987 | Evans |
| 5,173,389 | A | 12/1992 | Uenishi |
| 5,281,689 | A | 1/1994 | Bendler et al. |
| 5,565,300 | A | 10/1996 | Uenishi |
| 9,372,404 | B2* | 6/2016 | Watanabe ............... G03F 7/094 |
| 2002/0156189 | A1 | 10/2002 | Ogura |
| 2004/0254327 | A1* | 12/2004 | Boyles ................... C07C 17/093 528/86 |
| 2005/0255712 | A1 | 11/2005 | Kato et al. |
| 2007/0059632 | A1 | 3/2007 | Oguro |
| 2008/0044757 | A1 | 2/2008 | De Silva et al. |
| 2008/0113294 | A1 | 5/2008 | Echigo |
| 2008/0153031 | A1* | 6/2008 | Echigo ................... G03F 7/0382 430/281.1 |
| 2009/0081582 | A1 | 3/2009 | Hattori |
| 2010/0316950 | A1 | 12/2010 | Oguro et al. |
| 2011/0177459 | A1* | 7/2011 | Ogihara ................ B82Y 10/00 430/323 |
| 2012/0064725 | A1* | 3/2012 | Kinsho ................... G03F 7/091 438/703 |
| 2012/0171611 | A1 | 7/2012 | Ideno et al. |
| 2013/0302990 | A1* | 11/2013 | Watanabe ............... G03F 7/094 438/703 |
| 2014/0065533 | A1 | 3/2014 | Wu et al. |
| 2014/0186776 | A1 | 7/2014 | Uchiyama |
| 2014/0224765 | A1 | 8/2014 | Minegishi |
| 2014/0248561 | A1 | 9/2014 | Echigo |
| 2014/0308615 | A1 | 10/2014 | Echigo |
| 2014/0349222 | A1 | 11/2014 | Shibui |
| 2015/0037735 | A1* | 2/2015 | Yang ....................... C07C 69/96 430/281.1 |
| 2015/0212418 | A1 | 7/2015 | Nishimaki et al. |
| 2016/0068709 | A1 | 3/2016 | Endo et al. |
| 2017/0073288 | A1* | 3/2017 | Makinoshima .......... C08G 8/04 |
| 2017/0349564 | A1 | 12/2017 | Toida |
| 2018/0029968 | A1 | 2/2018 | Toida et al. |
| 2018/0044270 | A1 | 2/2018 | Horiuchi |
| 2018/0081270 | A1 | 3/2018 | Echigo |
| 2018/0107113 | A1 | 4/2018 | Toida |

FOREIGN PATENT DOCUMENTS

| | | |
|---|---|---|
| CN | 101889247 A | 11/2010 |
| CN | 103304385 A | 9/2013 |
| CN | 103804196 A | 5/2014 |
| CN | 104557552 A | 4/2015 |
| DE | 1167854 B | 4/1964 |

(Continued)

OTHER PUBLICATIONS

Ihori et al., "Chiral zirconium catalysts using multidentate BINOL derivatives for catalytic enantioselective . . . ", JACS vol. 127 pp. 15528-15535 (2005).*

(Continued)

*Primary Examiner* — Martin J Angebranndt
(74) *Attorney, Agent, or Firm* — Fitch, Even, Tabin & Flannery LLP

(57) ABSTRACT

The resist composition according to the present invention contains a compound represented by a specific formula. The compound has high heat resistance attributed to its highly aromatic skeleton, in spite of its low molecular weight, and may be used even under high temperature baking conditions. By virtue of the above configuration, the resist composition according to the present invention is excellent in heat resistance, has high solubility in a safe solvent, has high sensitivity, and can impart a good shape to a resist pattern. That is, the resist composition according to the present invention is useful as an acid amplification type non-polymer based resist material.

8 Claims, No Drawings

(56) References Cited

FOREIGN PATENT DOCUMENTS

| | | | |
|---|---|---|---|
| EP | 0 395 049 A1 | 10/1990 | |
| EP | 0 440 238 A2 | 8/1991 | |
| EP | 0604056 A2 | 6/1994 | |
| EP | 2660257 A1 | 11/2013 | |
| EP | 2 743 770 A1 | 6/2014 | |
| EP | 3118183 A1 | 1/2017 | |
| EP | 3118684 A1 | 1/2017 | |
| JP | S54-037492 B1 | 11/1979 | |
| JP | 02-285351 | * 11/1990 | |
| JP | 03-228057 | * 10/1991 | |
| JP | H04297430 A | 10/1992 | |
| JP | H05019463 A | 1/1993 | |
| JP | H05-067701 A | 3/1993 | |
| JP | H06242601 A | 9/1994 | |
| JP | 07-271037 | * 10/1995 | |
| JP | 08-137100 | * 5/1996 | |
| JP | H09106070 A | 4/1997 | |
| JP | H10-161332 A | 6/1998 | |
| JP | 10-307384 | * 11/1998 | |
| JP | 2001-122828 | * 5/2001 | C07C 43/23 |
| JP | 2002275112 A | 9/2002 | |
| JP | 2002-334869 A | 11/2002 | |
| JP | 2004-177668 A | 6/2004 | |
| JP | 2004-271838 A | 9/2004 | |
| JP | 2005-187335 | * 7/2005 | C07C 261/02 |
| JP | 2005-250434 A | 9/2005 | |
| JP | 2005266741 A | 9/2005 | |
| JP | 2005-326838 | * 11/2005 | |
| JP | 2005-326838 A | 11/2005 | |
| JP | 2006259482 A | 9/2006 | |
| JP | 2006-276742 A | 10/2006 | |
| JP | 2007-204574 A | 8/2007 | |
| JP | 2007-226170 A | 9/2007 | |
| JP | 2007-226204 A | 9/2007 | |
| JP | 2007-241271 A | 9/2007 | |
| JP | 2008-145539 A | 6/2008 | |
| JP | 2009080203 A | 4/2009 | |
| JP | 2009-173623 A | 8/2009 | |
| JP | 2010077038 A | 4/2010 | |
| JP | 2012-077295 | * 4/2012 | G03F 7/11 |
| JP | 2012083731 A | 4/2012 | |
| SG | 11201607444V A | 10/2016 | |
| WO | 2004037879 A2 | 5/2004 | |
| WO | 2004/066377 A1 | 8/2004 | |
| WO | 2005101127 A1 | 10/2005 | |
| WO | 2009/072465 A1 | 6/2009 | |
| WO | 2011/034062 A1 | 3/2011 | |
| WO | 2012153991 A2 | 11/2012 | |
| WO | 2012165507 A1 | 12/2012 | |
| WO | 2013024777 A1 | 2/2013 | |
| WO | 2013/036546 A2 | 3/2013 | |
| WO | 2013/134997 A1 | 9/2013 | |
| WO | 2014/024836 A1 | 2/2014 | |
| WO | 2015/137486 A1 | 9/2015 | |
| WO | 2015137485 A1 | 9/2015 | |
| WO | 2016/129679 | * 8/2016 | |
| WO | 2016/158456 | * 10/2016 | |
| WO | 2016/163456 | * 10/2016 | |
| WO | 2017/038979 | * 3/2017 | |
| WO | 2017/043561 | * 3/2017 | |

OTHER PUBLICATIONS

Sundberg et al., "Visualization of the develop process", Proc. SPIE vol. 7972, 79720I (10 pages) (2011).*

T. Nakayama, M. Nomura, K. Haga, M. Ueda: Bull. Chem. Soc. Jpn., 71, 1979 (1998).

De Silva, Anuja; Forman, Drew; Ober, Christopher K., Molecular glass resists for EUV lithography, Proceedings of SPIE—The International Society for Optical Engineering (Pt. 2, Advances in Resist Technology and Processing XXIII), 2006, 6153, 615341/1-615341/10.

Sundberg, Linda K.; Wallraff, Gregory M.; Friz, Alexander M.; Davis, Blake W.; Swanson, Sally A.; Brock, Phillip J.; Rettner, Charles T.; Hinsberg, William D., Visualization of the develop process, Proceedings of SPIE (Advances in Resist Materials and Processing Technology XXVIII), 2011, 7972, 797201/1-797201/10.

Arai, Tadashi; Hattori, Takashi; Shiraishi, Hiroshi; Fukuda, Hiroshi, Polyphenol-based positive-tone EB resist: Resist shade mask, Journal of Photopolymer Science and Technology, 2004, 17(4), 567-573.

Schultz, Andreas et al., Tetraphenylethene-derived columnar liquid crystals and their oxidative photocyclization, European Journal of Organic Chemistry, 2003, (15), p. 2829-2839, p. 2832, scheme 4, compound 17.

Reddy, D. Shekhar et al., Charge-transfer diamondoid lattices: an unprecedentedly huge and highly catenating diamondoid network arising from a tetraphenol as a tetrahedral node and benzoquinone as a linear spacer, Angewandte Chemie, International Edition, 2000, 39(23), p. 4266-4268, scheme 1, compound 1.

Vogl, Erasmus M. et al., Linking BINOL: C2-symmetric ligands for investigations on asymmetric catalysis, Tetrahedron Letters, 1998, 39(43), p. 7917-7920, pp. 7918 to 7919, compounds 2, 9.

Steven A. Hardinger, "Methine Group", Illustrated Glossary of Organic Chemistry, Department of Chemistry & Biochemistry, UCLA, copyright 2010-2017, 2 pages downloaded Feb. 16, 2018.

James, "9 Nomenclature Conventions to Know", Master Organic Chemistry, copyright 2018, 26 pages downloaded Feb. 15, 2018.

Cammack et al. (2006). Oxford Dictionary of Biochemistry and Molecular Biology (2nd Edition). Oxford University Press. pp. 419, 422.

Boyles, David A., et al., "Synthesis of High Aspect Ratio Bisphenols and Polycarbonates Incorporating Bisaryl Units," Macromolecules, 2005, 38 (9), pp. 3362-3629, DOI: 10.1021/ma048616m Publication Date (Web): Mar. 30, 2005.

Amaya, Toru, Miyasaka, Akihiro, and Hirao, Toshikazu, "Synthesis of three-dimensionally arranged bis-biphenol ligand on hexaarylbenzene scaffold and its application for cross-pinacol coupling reaction," Tetrahedron Letters, Jul. 2, 2011, vol. 52, pp. 4567-4569.

Cantin, Katy, et al. "Studies Toward the Synthesis of Phenylacetylene Macrocycle Based Rotaxane Precursors as Building Blocks for Organic Nanotubes," European Journal of Organic Chemistry, 2012, pp. 5335-5349.

Chaumont, Clement, et al., "Synthesis, topology and energy analysis of crystaline resorcinol-based oligophenylene molecules with various symmetries," CrystEngComm, vol. 15, No. 34, Jan. 2013, pp. 6845-6862.

Chen, Huanqing, et al., "Biphen[n]arenes," Chemical Science; vol. 6, No. 197; the Royal Society of Chemistry; 2015; pp. 197-202.

Ghebremariam, Bereket, and Matile, Stefan, "Synthesis of Asymmetric Septi-(p-Phenylene)s," Tetrahedron Letters, May 13, 1998, vol. 39, pp. 5335-5338.

Jang, Cheong-Jin, Ryu, Ja-Hyoung, Lee, Joon-Dong, Sohn, Deawon, and Lee Myongsoo, "Synthesis and Supramolecular Nanostructure of Amphiphilic Rigid Aromatic-Flexible Dendritic Block Molecules," Chemistry of Materials, Sep. 10, 2004, vol. 16, pp. 4226-4231.

Lin, Ying, et al., "Palladium-Catalyzed [3+2] Cycloaddition Reaction of (Diarylmethylene)-cyclopropa[b]naphthalenes with Arynes: An Efficient Synthesis of 11-(Diarylmethylene)-11H-benzo[b]fluorenes," European Journal of Organic Chemistry, vol. 2011, No. 16, Jan. 2011, pp. 2993-3000.

Pegenau, Annegret, et al., "The Importance of Micro Segregation for Mesophase Formation: Thermotropic Columnar Mesophases of Tetrahedral and other Low-Aspect-Ratio Organic Materials," Chem. Eur. J., vol. 5, No. 5, May 1999, pp. 1643-1660.

Rathore, Rajendra, Burns, Carrie L., and Deselnicu, Mihaela I., "Multiple-Electron Transfer in a Single Step. Design and Synthesis of Highly Charged Cation-Radical Salts," Organic Letters, Sep. 1, 2001, vol. 3, No. 18, pp. 2887-2890.

Ryu, Ja-Hyoung, et al.," Self-Assembling Molecular Dumbbells: From Nanohelices to Nanocapsules Triggered by Guest Intercalation," Angewandte Chemie International Edition, vol. 45, No. 32, 2006, pp. 5304-5307.

(56) References Cited

OTHER PUBLICATIONS

Yamada, Arisa, et al.; Development of High Resolution Molecular Resist Based on Tris((hydroxypheny)pheny)benzene; Journal of Photopolymer Science and Technology; vol. 23, No. 1; 2010; pp. 91-95.

* cited by examiner

RESIST COMPOSITION AND METHOD FOR FORMING RESIST PATTERN

CROSS-REFERENCE TO RELATED APPLICATIONS

This application is a U.S. national phase application filed under 35 U.S.C. § 371 of International Application PCT/JP2015/057470, filed on Mar. 13, 2015, designating the United States, which claims priority from Japanese Application Number 2014-050767, filed Mar. 13, 2014, which are hereby incorporated herein by reference in their entirety.

TECHNICAL FIELD

The present invention relates to a resist composition and a method for forming a resist pattern using the resist composition.

BACKGROUND ART

Conventional typical resist materials are polymer based materials capable of forming amorphous thin films. For example, a line pattern of about 45 to 100 nm is formed by irradiating a resist thin film made by coating a substrate with a solution of a polymer resist material such as polymethyl methacrylate, polyhydroxy styrene with an acid dissociation reactive group, or polyalkyl methacrylate with ultraviolet, far ultraviolet, electron beam, extreme ultraviolet (EUV), and X-ray or the like.

However, because polymer based resists have a molecular weight as large as about 10,000 to 100,000 and also wide molecular weight distribution, in lithography using a polymer based resist, roughness occurs on a fine pattern surface; the pattern dimension becomes difficult to be controlled; and the yield decreases. Therefore, there is a limitation in miniaturization with lithography using a conventional polymer based resist material. In order to make a finer pattern, various low molecular weight resist materials have been proposed.

For example, an alkaline development type negative type radiation-sensitive composition (see Patent Literatures 1 and 2) using a low molecular weight polynuclear polyphenolic compound as a main component has been suggested.

As a candidate of a low molecular weight resist material having high heat resistance, an alkaline development type negative type radiation-sensitive composition (see Patent Literature 3 and Non Patent Literature 1) using a low molecular weight cyclic polyphenolic compound as a main component has been suggested.

CITATION LIST

Patent Literature

Patent Literature 1: Japanese Patent Application Laid-Open No. 2005-326838
Patent Literature 2: Japanese Patent Application Laid-Open No. 2008-145539
Patent Literature 3: Japanese Patent Application Laid-Open No. 2009-173623

Non Patent Literature

Non Patent Literature 1: T. Nakayama, M. Nomura, K. Haga, M. Ueda: Bull. Chem. Soc. Jpn., 71, 2979 (1998)

SUMMARY OF INVENTION

However, the techniques described in Patent Literatures 1 and 2 have the disadvantages that the heat resistance of the obtained composition is not sufficient and the shape of the resulting resist pattern becomes poor. Also, the techniques described in Patent Literature 3 and Non Patent Literature 1 have problems such as low solubility in a safe solvent used in a semiconductor production process, low sensitivity, and the poor shape of the resulting resist pattern. Such low molecular weight resist materials obtained by the conventional techniques are still susceptible to improvement.

The present invention has been made in light of the problems of the conventional techniques described above, and an object of the present invention is to provide a resist composition which is excellent in heat resistance, has high solubility in a safe solvent, has high sensitivity, and can impart a good shape to a resist pattern, and a method for forming a resist pattern using the resist composition.

The inventors have, as a result of devoted examinations to solve the above problems, found out that by containing a compound having a specific structure, a resist composition is excellent in heat resistance, has high solubility in a safe solvent, has high sensitivity, and can impart a good shape to a resist pattern, and reached the present invention. More specifically, the present invention is as follows.

[1] A resist composition comprising a compound represented by the following formula (1):

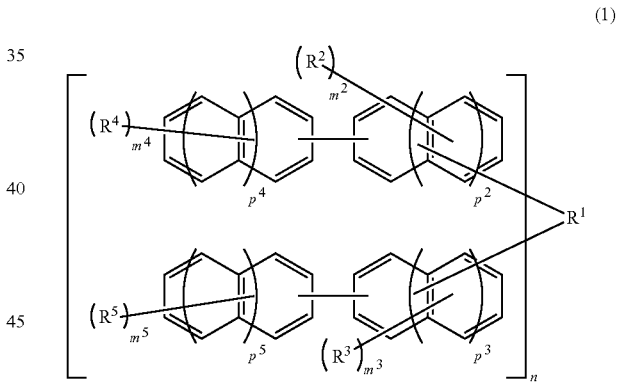

(1)

wherein $R^1$ is a 2n-valent group having 1 to 30 carbon atoms; $R^2$ to $R^5$ are each independently a linear, branched or cyclic alkyl group having 1 to 10 carbon atoms, an aryl group having 6 to 10 carbon atoms, an alkenyl group having 2 to 10 carbon atoms, a thiol group, or a hydroxyl group, wherein at least one of $R^4$ and/or at least one of $R^5$ is a hydroxyl group and/or a thiol group; $m^2$ and $m^3$ are each independently an integer of 0 to 8; $m^4$ and $m^5$ are each independently an integer of 0 to 9, wherein at least one of $m^4$ and $m^5$ is an integer of 1 to 9; n is an integer of 1 to 4; and $p^2$ to $p^5$ are each independently an integer of 0 to 2.

[2] The resist composition according to [1], wherein at least one of $R^2$ and/or at least one of $R^3$ is a hydroxyl group and/or a thiol group.

[3] The resist composition according to [1] or [2], wherein the compound represented by the formula (1) is a compound represented by the following formula (1a):

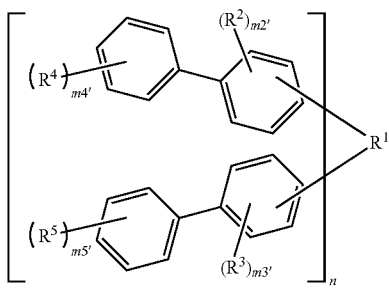

(1a)

wherein $R^1$ to $R^5$ and n are the same as defined in the formula (1); $m^{2'}$ and $m^{3'}$ are each independently an integer of 0 to 4; and $m^{4'}$ and $m^{5'}$ are each independently an integer of 0 to 5, wherein at least one of $m^{4'}$ and $m^{5'}$ is an integer of 1 to 5.

[4] The resist composition according to any of [1] to [3], wherein n is 1, and $R^1$ is a group represented by $R^A$-$R^B$, wherein $R^A$ is a methine group, and $R^B$ is an aryl group having 7 or more carbon atoms.

[5] The resist composition according to [3], wherein the compound represented by the formula (1a) is a compound represented by the following formula (1b):

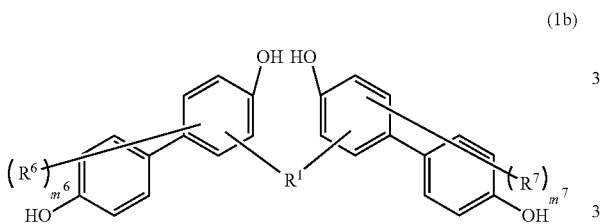

(1b)

wherein $R^1$ is the same as defined in the formula (1); $R^6$ and $R^7$ are each independently a linear, branched or cyclic alkyl group having 1 to 10 carbon atoms, an aryl group having 6 to 10 carbon atoms, an alkenyl group having 2 to 10 carbon atoms, a thiol group, or a hydroxyl group; and $m^6$ and $m^7$ are each independently an integer of 0 to 7.

[6] The resist composition according to [5], wherein the compound represented by the formula (1b) is a compound represented by the following formula (BiF-1):

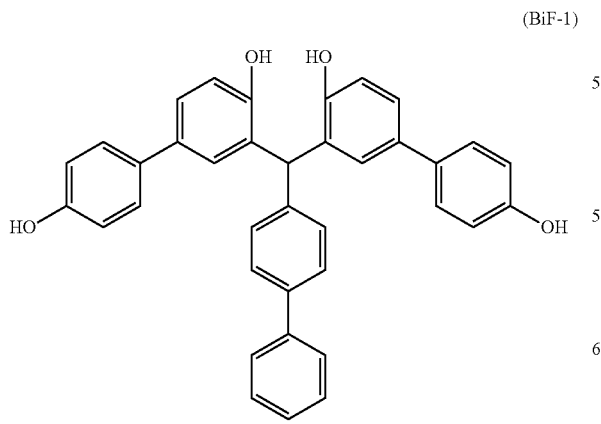

(BiF-1)

[7] The resist composition according to any of [1] to [6], further comprising a solvent.

[8] The resist composition according to any of [1] to [7], further comprising an acid generating agent.

[9] The resist composition according to any of [1] to [8], further comprising an acid crosslinking agent.

[10] A method for forming a resist pattern, comprising the steps of:

coating a substrate with the resist composition according to any of [1] to [9], thereby forming a resist film;
exposing the formed resist film; and
developing the exposed resist film.

The resist composition of the present invention is excellent in heat resistance, has high solubility in a safe solvent, has high sensitivity, and can impart a good shape to a resist pattern.

DESCRIPTION OF EMBODIMENTS

Hereinafter, an embodiment of the present invention (hereinafter, referred to as "present embodiment") will be described. The present embodiment is given in order to illustrate the present invention. The present invention is not limited to only the present embodiment.

[Resist Composition]

The resist composition of the present embodiment comprises a compound represented by the following formula (1) (hereinafter, also referred to as compound (A)):

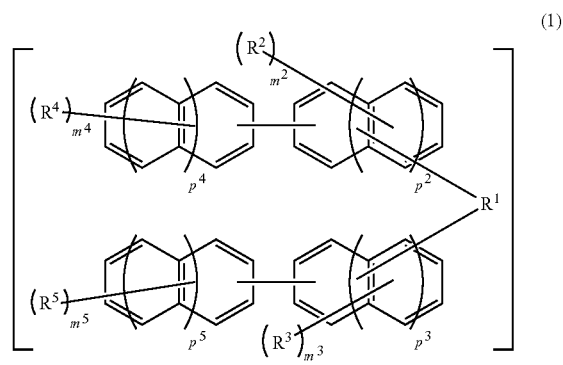

(1)

In the above formula (1), $R^1$ is a 2n-valent group having 1 to 30 carbon atoms. The compound (A) according to the present embodiment has a configuration in which each aromatic ring is bonded via this $R^1$.

$R^2$ to $R^5$ are each independently a monovalent group selected from the group consisting of a linear, branched or cyclic alkyl group having 1 to 10 carbon atoms, an aryl group having 6 to 10 carbon atoms, an alkenyl group having 2 to 10 carbon atoms, a thiol group, and a hydroxyl group. Herein, at least one of $R^4$ and/or at least one of $R^5$ is a hydroxyl group and/or a thiol group.

$m^2$ and $m^3$ are each independently an integer of 0 to 8, and $m^4$ and $m^5$ are each independently an integer of 0 to 9. Herein, at least one of $m^4$ and $m^5$ is an integer of 1 to 9. That is, $m^4$ and $m^5$ are not 0 at the same time.

n is an integer of 1 to 4.

$p^2$ to $p^5$ are each independently an integer of 0 to 2.

By virtue of the above configuration, the resist composition of the present embodiment is excellent in heat resistance, has high solubility in a safe solvent, has high sensitivity, and can impart a good shape to a resist pattern. That is, the resist composition of the present embodiment is useful as an acid amplification type non-polymer based resist material.

The above 2n-valent group refers to an alkylene group having 1 to 30 carbon atoms (n=1), an alkanetetrayl group having 1 to 30 carbon atoms (n=2), an alkanehexayl group having 2 to 30 carbon atoms (n=3), or an alkaneoctayl group having 3 to 30 carbon atoms (n=4). Examples of the 2n-valent group include ones having a linear hydrocarbon group, a branched hydrocarbon group, or a cyclic hydrocarbon group. Herein, the cyclic hydrocarbon group also includes bridged cyclic hydrocarbon groups. Also, the 2n-valent group may have an aromatic group having 6 to 30 carbon atoms.

The above 2n-valent group may have a double bond. Also, the group may have a heteroatom.

In the present embodiment, preferably, n is 1, and $R^1$ is a group represented by $R^A$-$R^B$, wherein $R^A$ is a methine group, and $R^B$ is an aryl group having 7 or more carbon atoms. In this case, etching resistance tends to be higher, and it tends to be possible to form a resist layer as a thinner film while rendering a resist pattern finer. Examples of the aryl group having 7 or more carbon atoms include, but not limited to, a biphenyl group, a naphthalene group, an anthracene group, and a pyrene group.

On the other hand, in the present embodiment, n is preferably an integer of 2 to 4 from the viewpoint of heat resistance.

The compound represented by the above formula (1) has high heat resistance attributed to its highly aromatic skeleton, in spite of its low molecular weight, and may be used even under high temperature baking conditions. Since the compound represented by the formula (1) has a low molecular weight and may be baked at a high temperature, the compound is highly sensitive and can impart a good shape to a resist pattern. In addition, the compound represented by the formula (1) is excellent in solvent solubility, is suitable for use in thick film resists, and has good storage stability as a resist solution. The compound represented by the formula (1) is excellent in solvent solubility in spite of its highly aromatic skeleton, presumably because a benzene ring, a naphthalene ring, or an anthracene ring is bonded through a single bond, resulting in high affinity for a solvent, though the present invention is not intended to be limited thereto. Herein, the molecular weight of the compound of the present embodiment is preferably 5000 or smaller, more preferably 4000 or smaller, and still more preferably 3000 or smaller. The molecular weight can be measured by a method described in Examples mentioned later.

In the compound represented by the above formula (1), at least one of $R^2$ and/or at least one of $R^3$ is preferably a hydroxyl group and/or a thiol group from the viewpoint of solubility in an organic solvent.

The compound represented by the above formula (1) is more preferably a compound represented by the following formula (1a) from the viewpoint of the supply of raw materials:

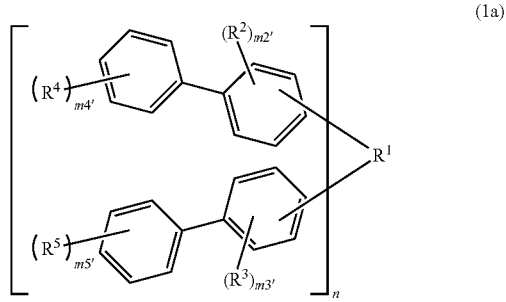

(1a)

In the above formula (1a), $R^1$ to $R^5$ and n are the same as defined in the formula (1).

$m^{2'}$ and $m^{3'}$ are each independently an integer of 0 to 4, and $m^{4'}$ and $m^{5'}$ are each independently an integer of 0 to 5. Herein, at least one of $m^{4'}$ and $m^{5'}$ is an integer of 1 to 5. That is, $m^{4'}$ and $m^{5'}$ are not 0 at the same time.

The compound represented by the above formula (1a) is still more preferably a compound represented by the following formula (1b) from the viewpoint of higher solubility in an organic solvent:

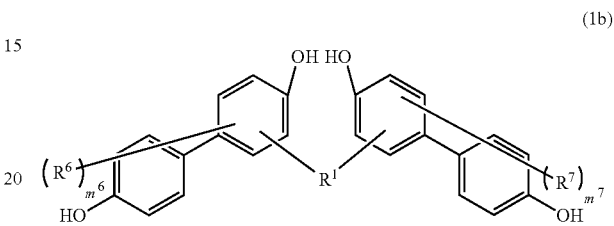

(1b)

In the above formula (1b), $R^1$ is the same as defined in the formula (1).

$R^6$ and $R^7$ are each independently a linear, branched or cyclic alkyl group having 1 to 10 carbon atoms, an aryl group having 6 to 10 carbon atoms, an alkenyl group having 2 to 10 carbon atoms, a thiol group, or a hydroxyl group.

$m^6$ and $m^7$ are each independently an integer of 0 to 7.

The compound represented by the above formula (1b) is further preferably a compound represented by the following formula (BiF-1) from the viewpoint of higher solubility in an organic solvent:

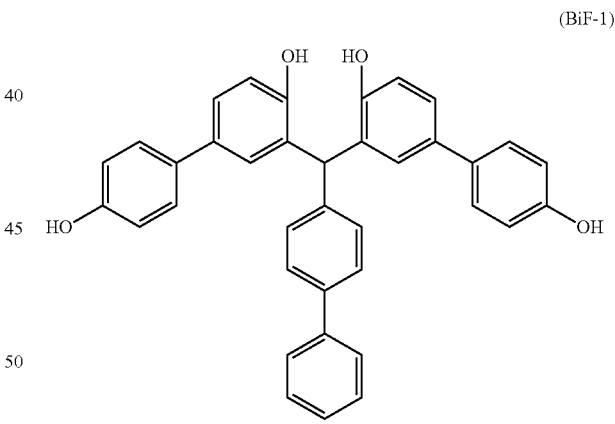

(BiF-1)

Specific examples of the compound represented by the above formula (1) include, but not limited to, the followings:

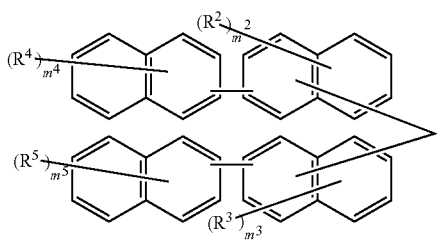

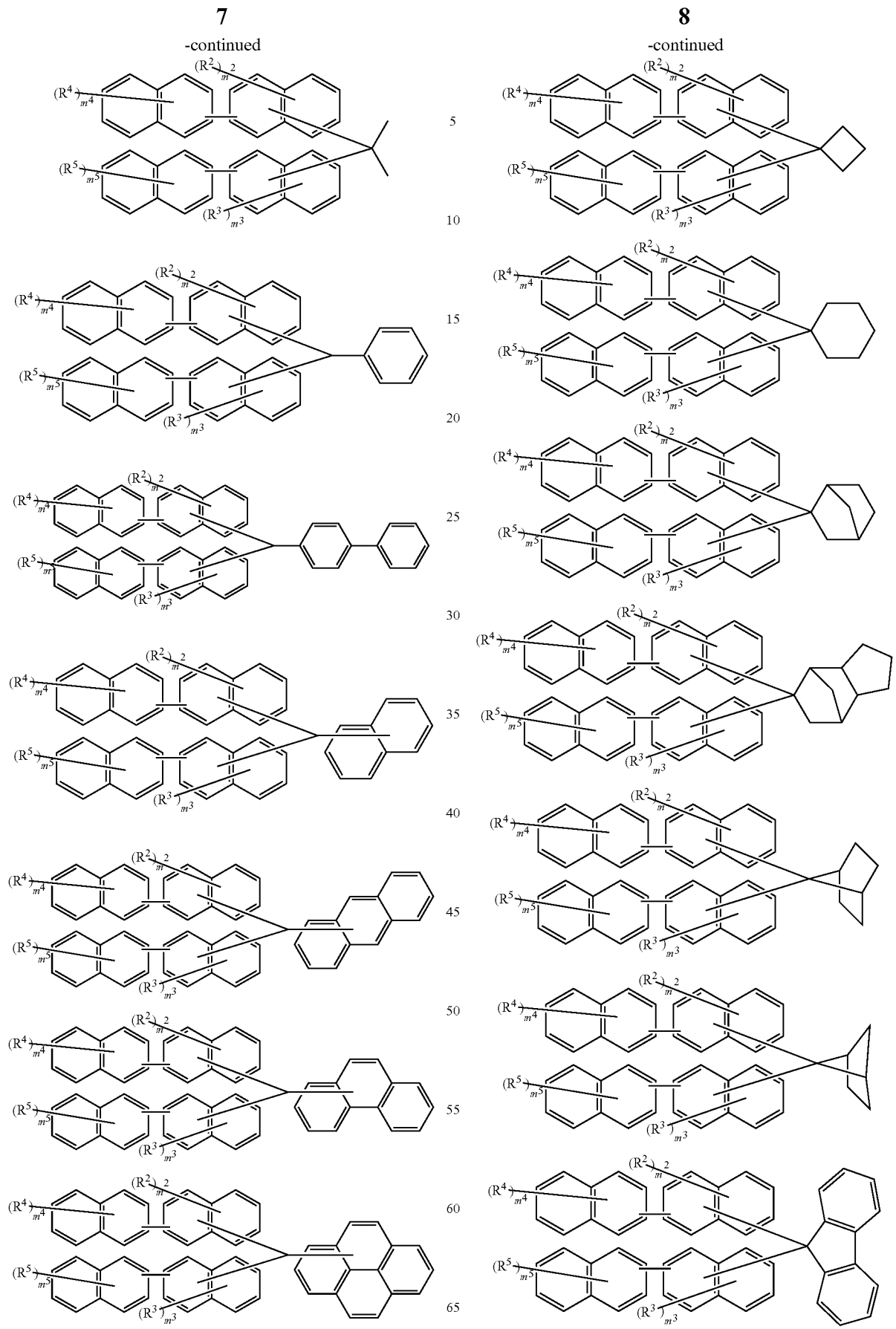

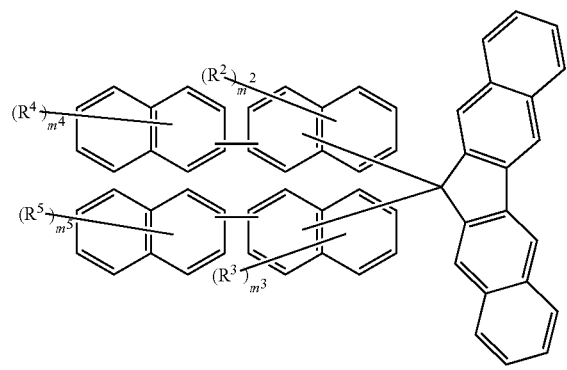
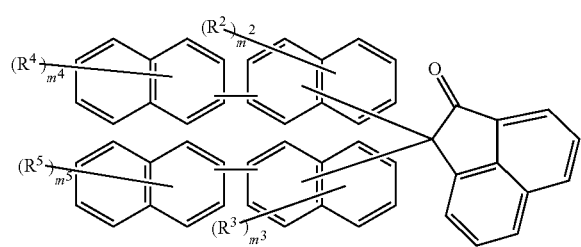
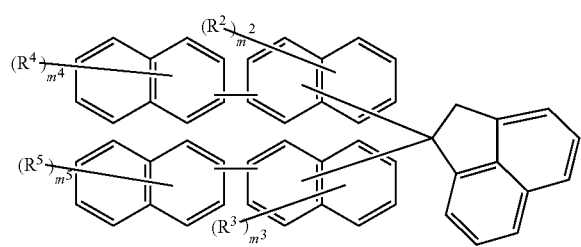
In the above compounds, $R^2$ to $R^5$ and $m^2$ to $m^5$ are the same as defined in the formula (1).
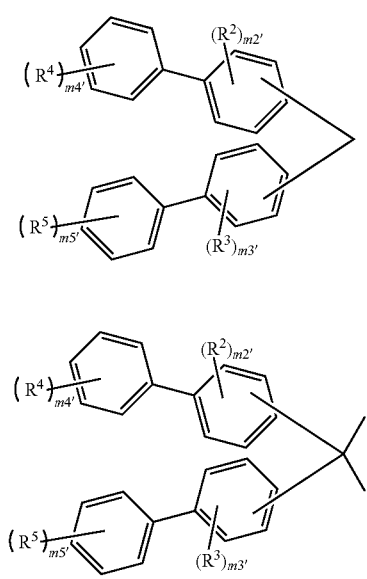
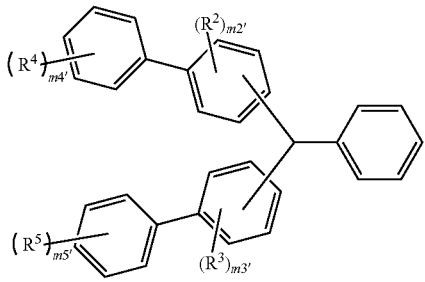
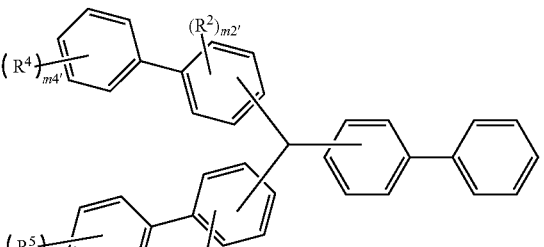
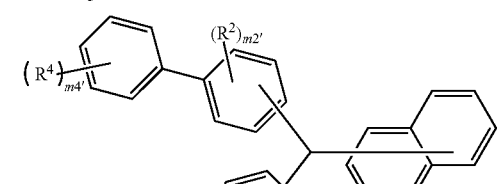
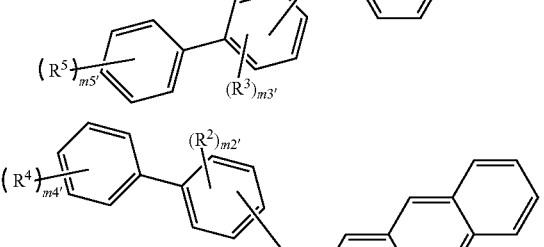
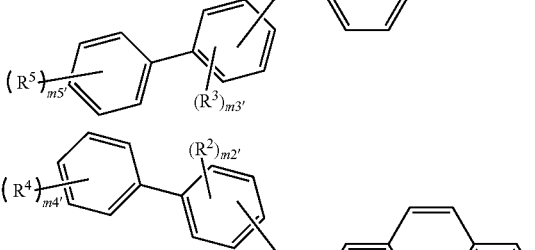
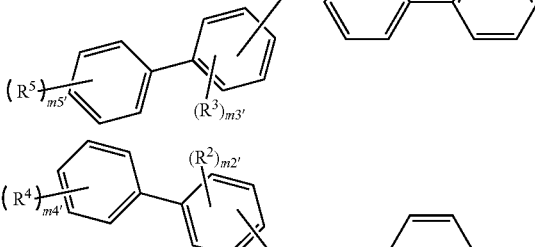

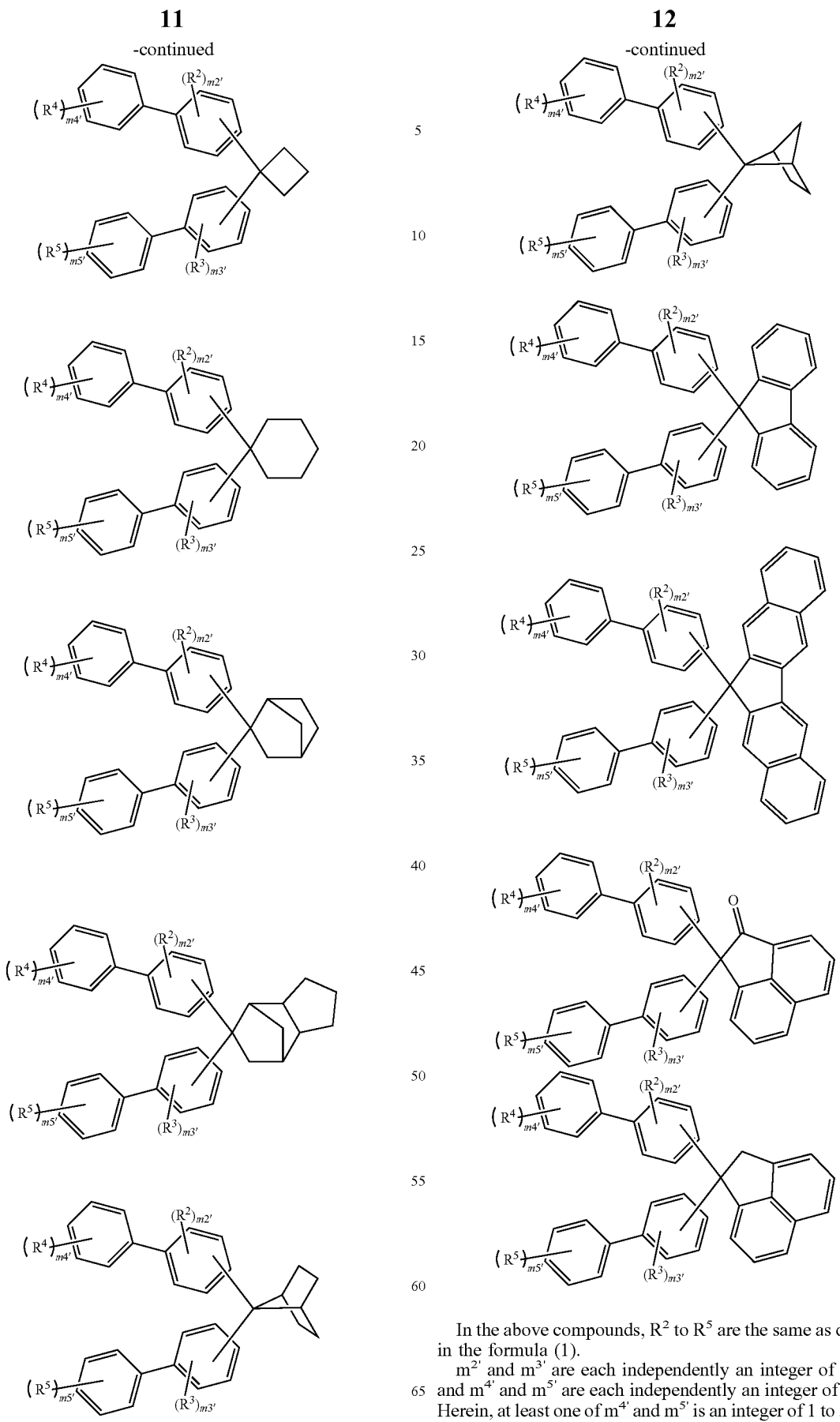
In the above compounds, $R^2$ to $R^5$ are the same as defined in the formula (1).
$m^{2'}$ and $m^{3'}$ are each independently an integer of 0 to 4, and $m^{4'}$ and $m^{5'}$ are each independently an integer of 0 to 5. Herein, at least one of $m^{4'}$ and $m^{5'}$ is an integer of 1 to 5. That is, $m^{4'}$ and $m^{5'}$ are not 0 at the same time.

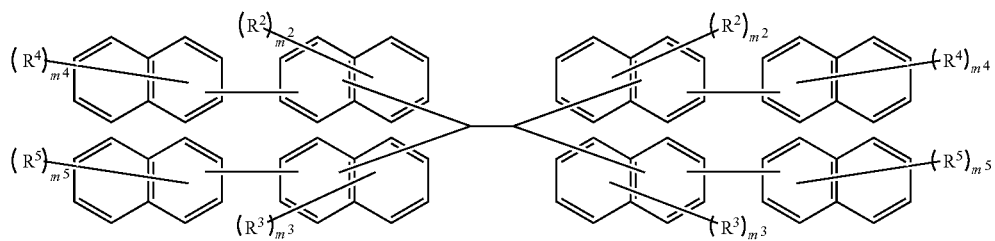
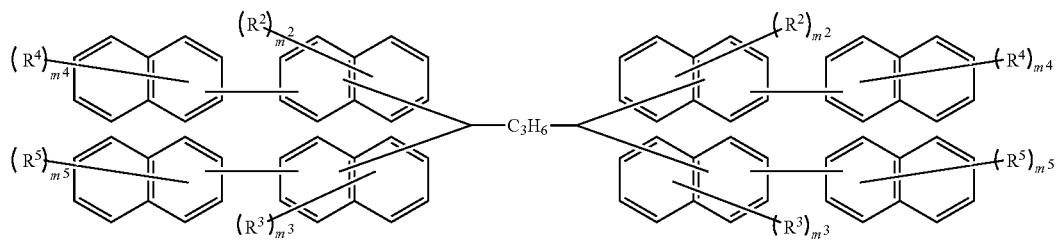
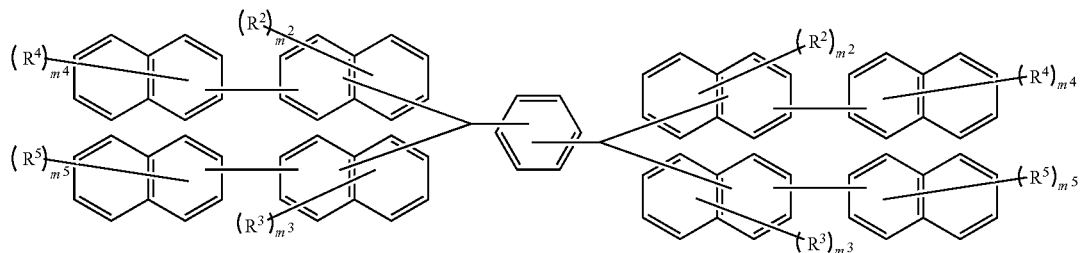
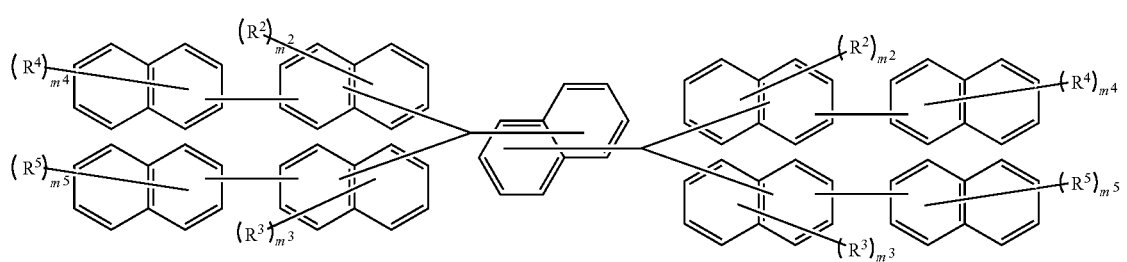
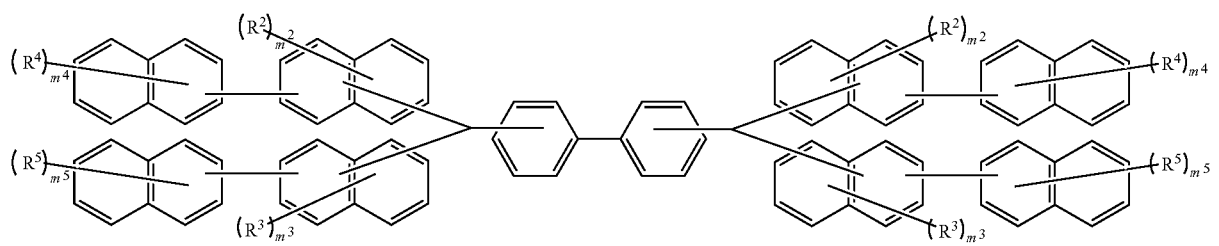
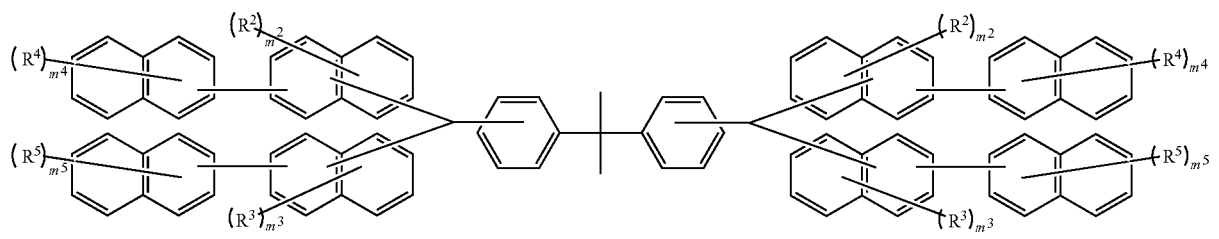

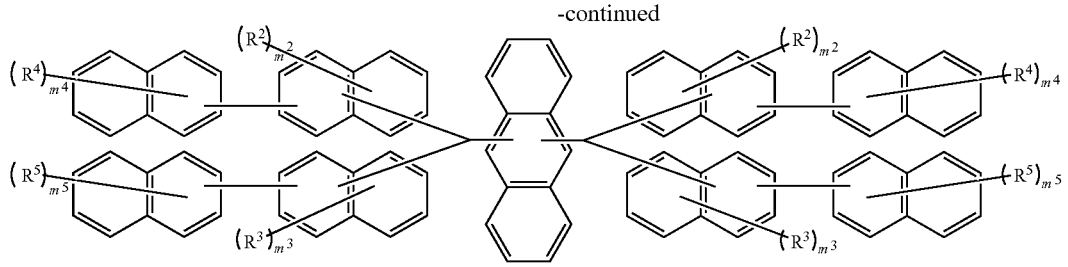
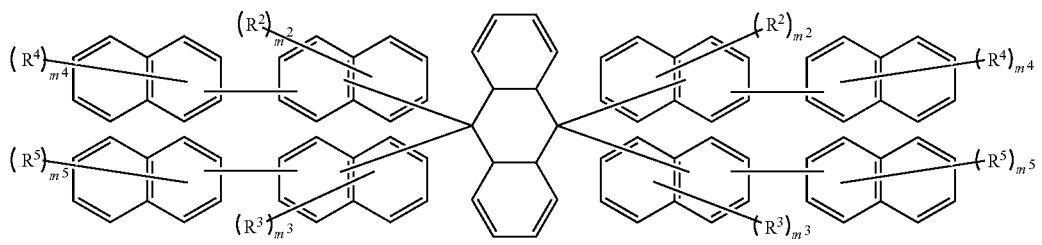
In the above compounds, $R^2$ to $R^5$ and $m^2$ to $m^5$ are the same as defined in the formula (1).
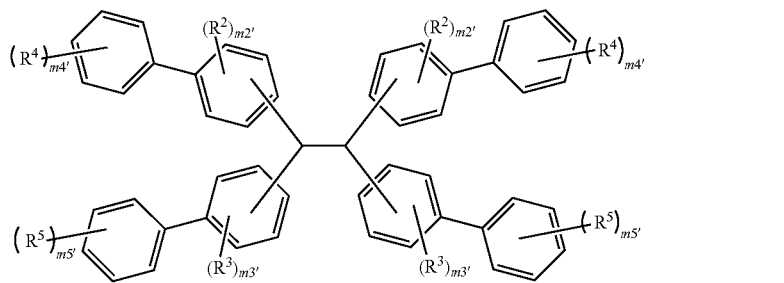
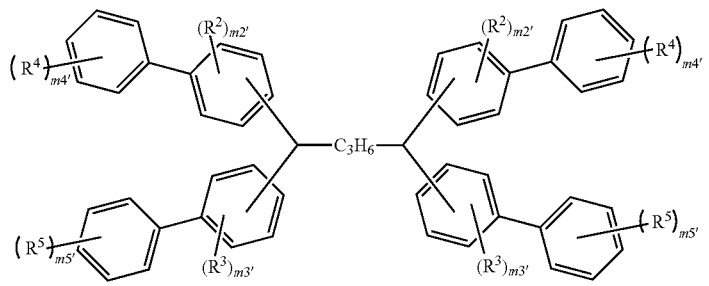
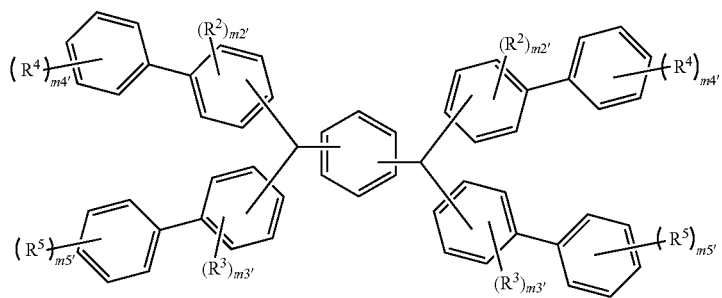

-continued
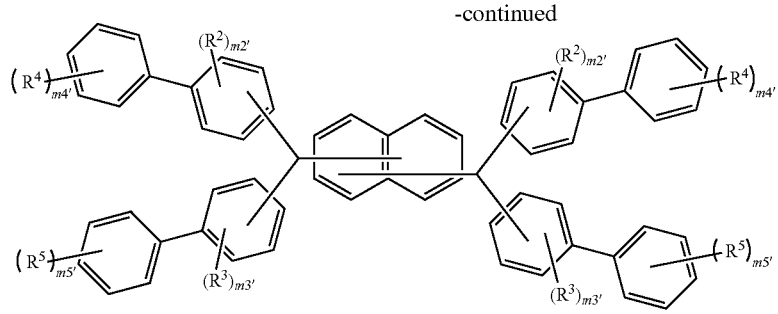
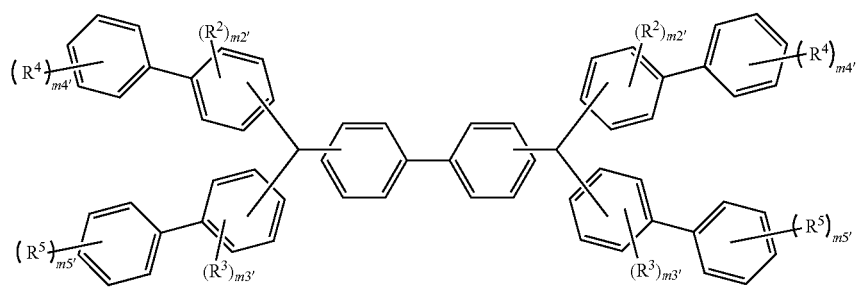
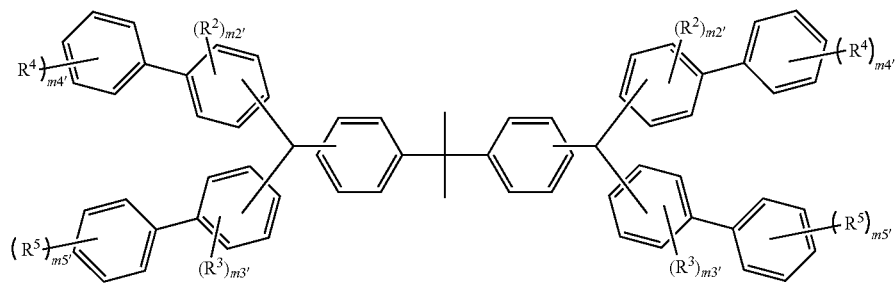
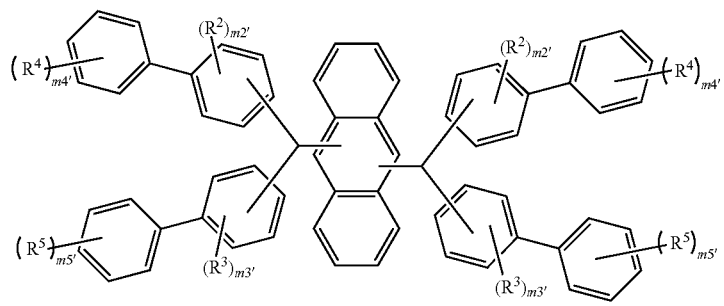
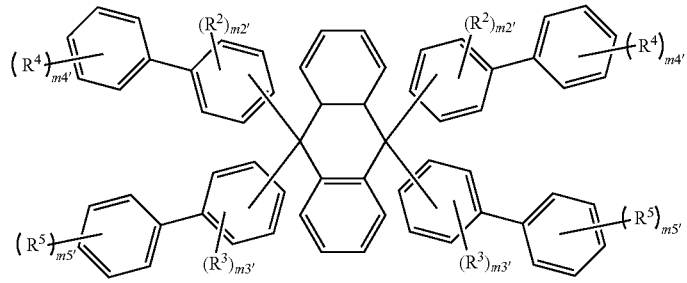
In the above compounds, $R^2$ to $R^5$ are the same as defined in the formula (1).

$m^{2'}$ and $m^{3'}$ are each independently an integer of 0 to 4, and $m^{4'}$ and $m^{5'}$ are each independently an integer of 0 to 5.
Herein, at least one of $m^{4'}$ and $m^{5'}$ is an integer of 1 to 5. That is, $m^{4'}$ and $m^{5'}$ are not 0 at the same time.
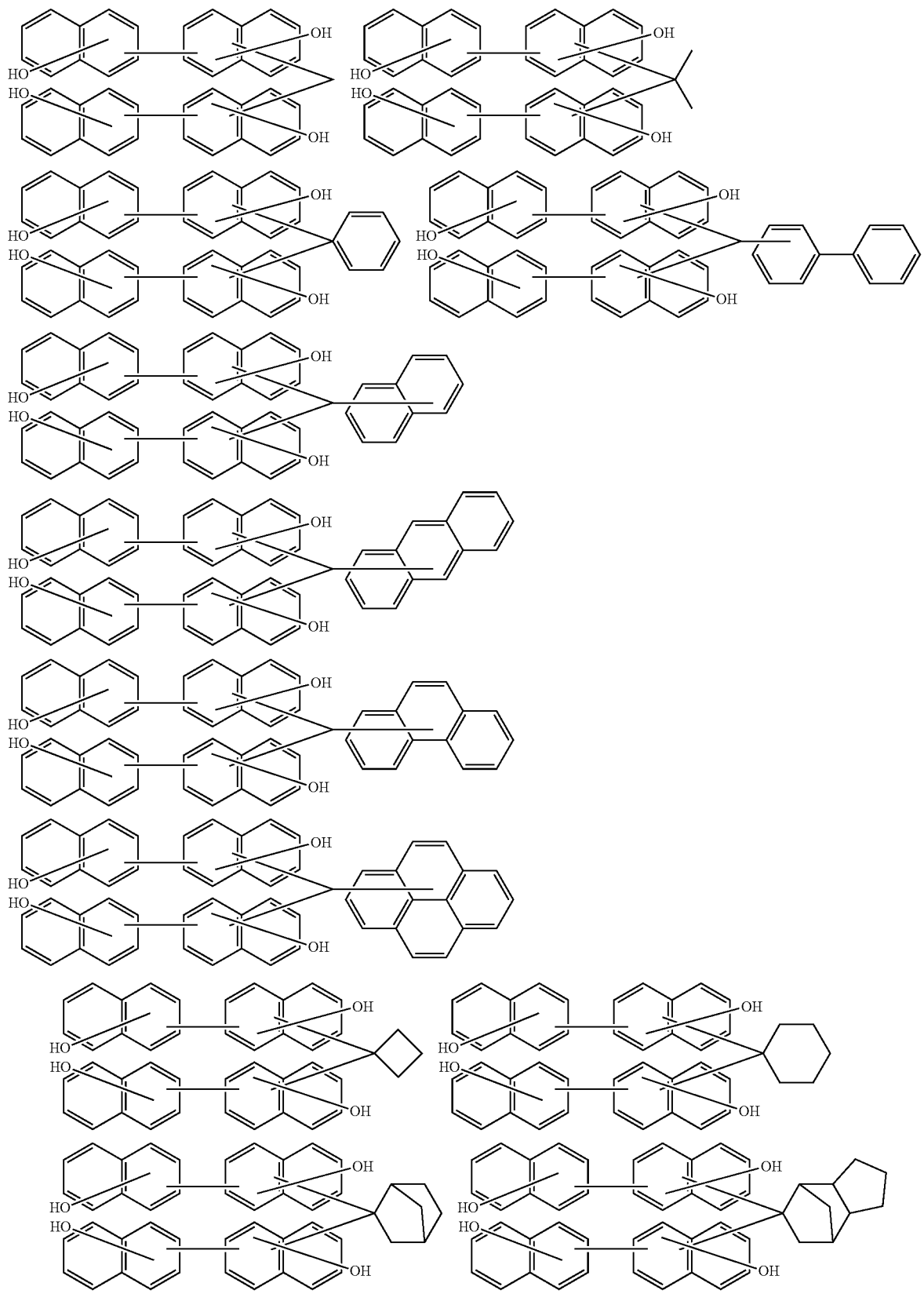

-continued
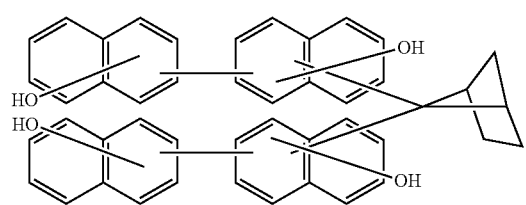
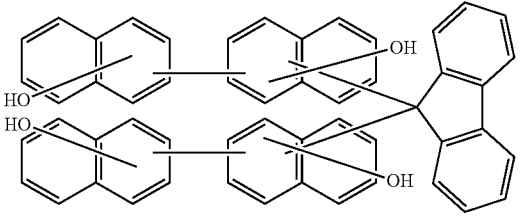
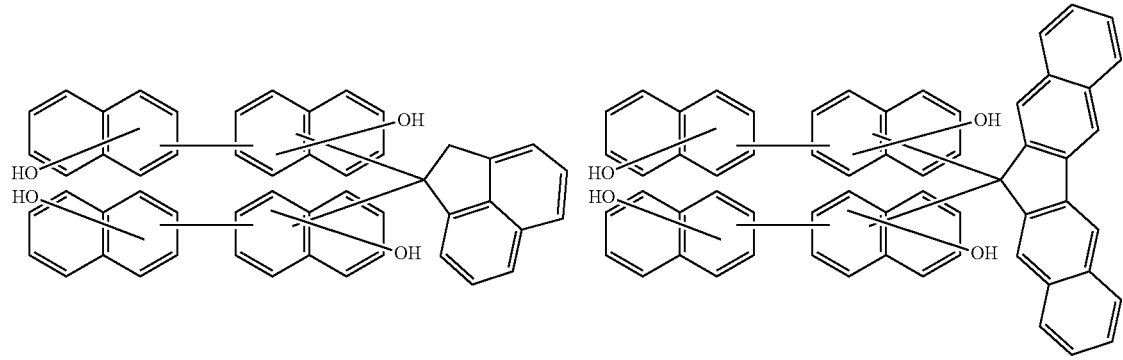
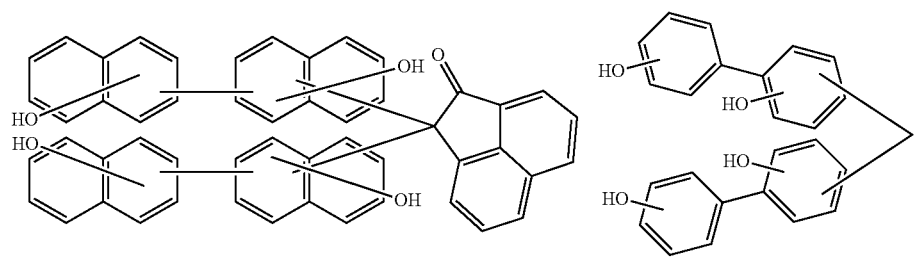
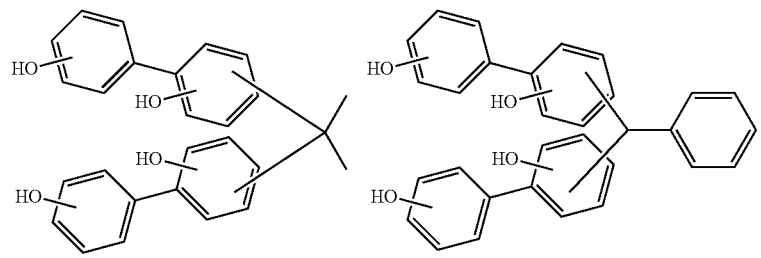
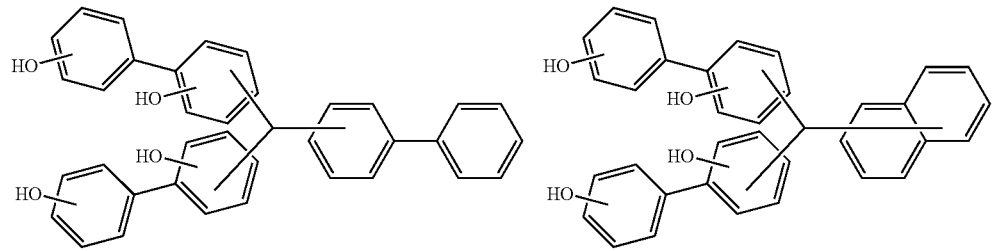
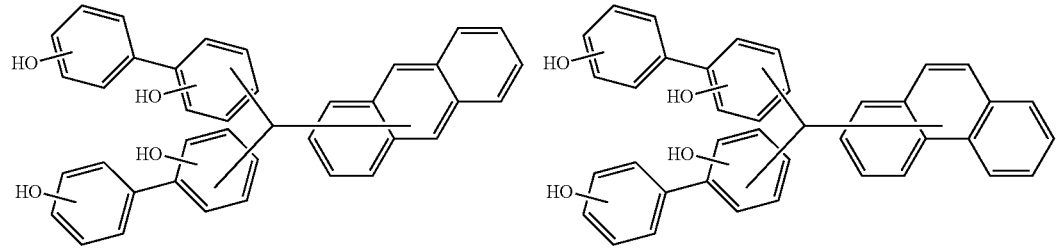

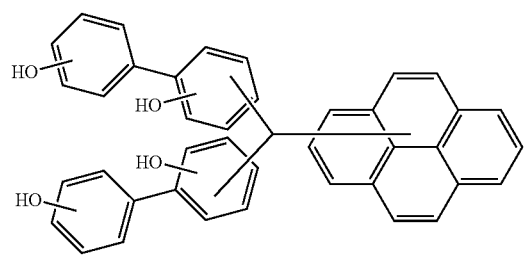
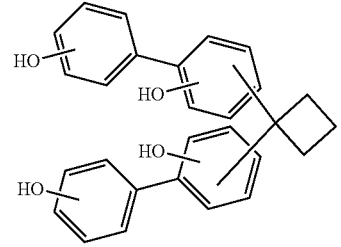
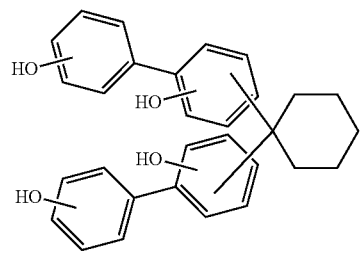
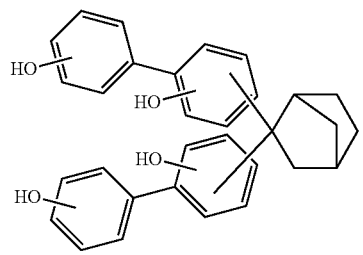
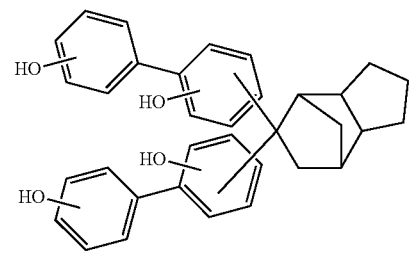
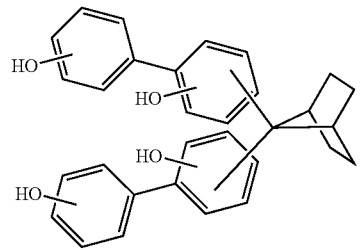
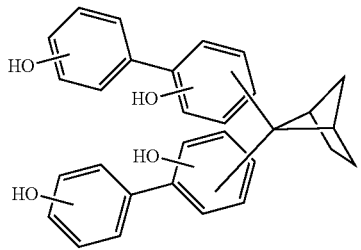
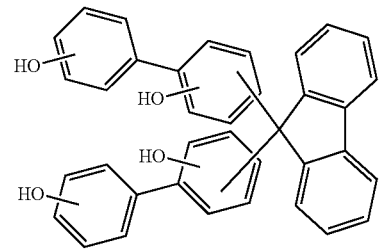
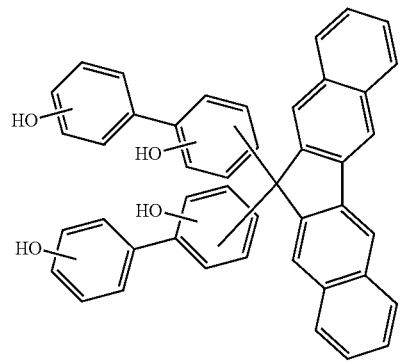
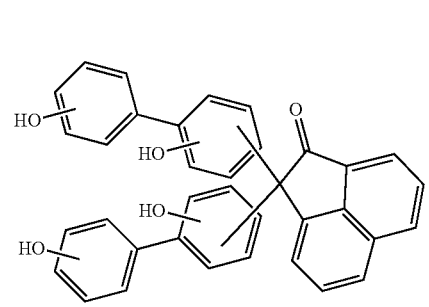
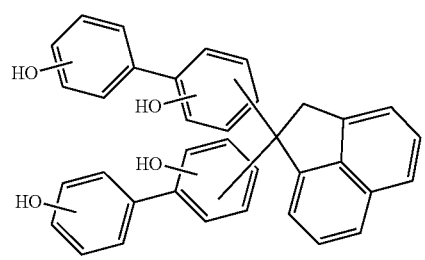
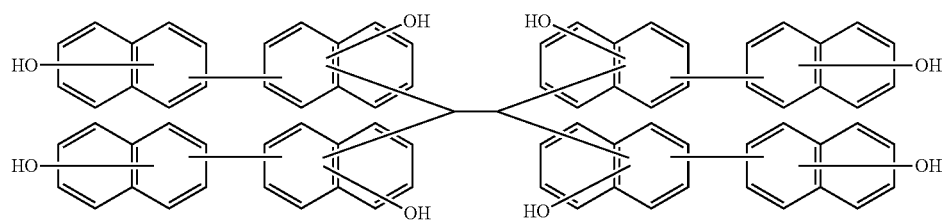

-continued
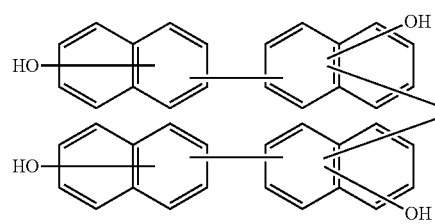
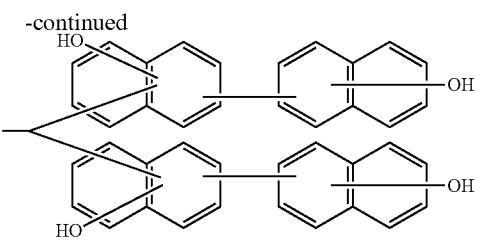
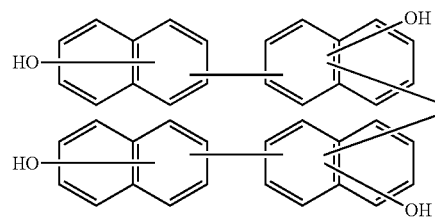
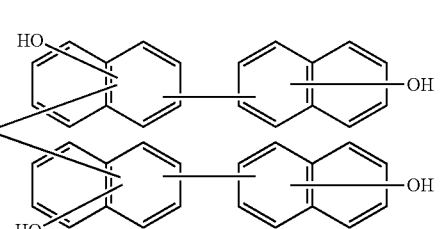
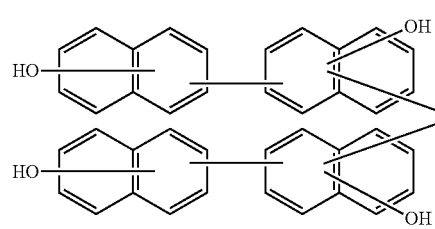
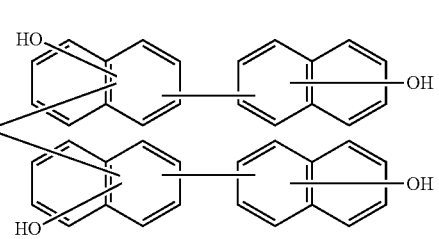
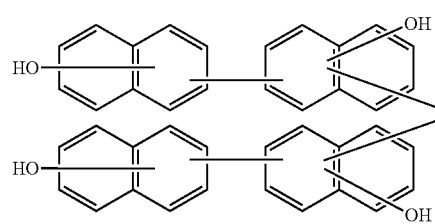
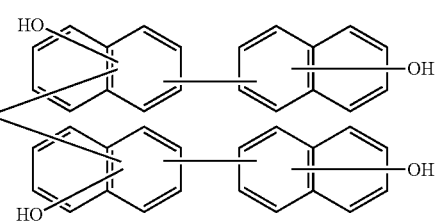
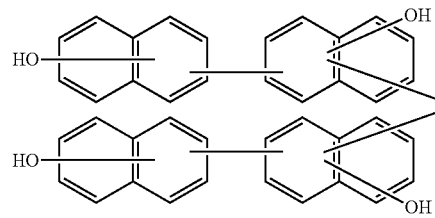
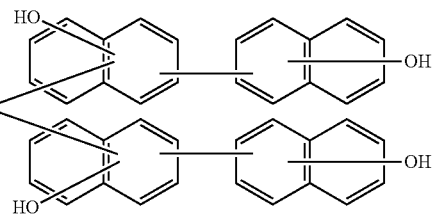
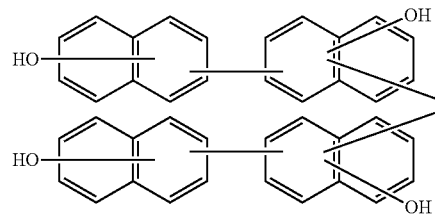
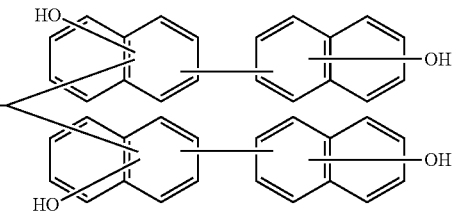
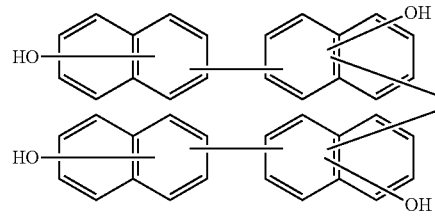
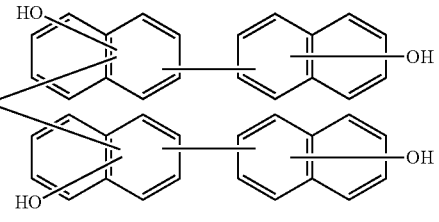

-continued
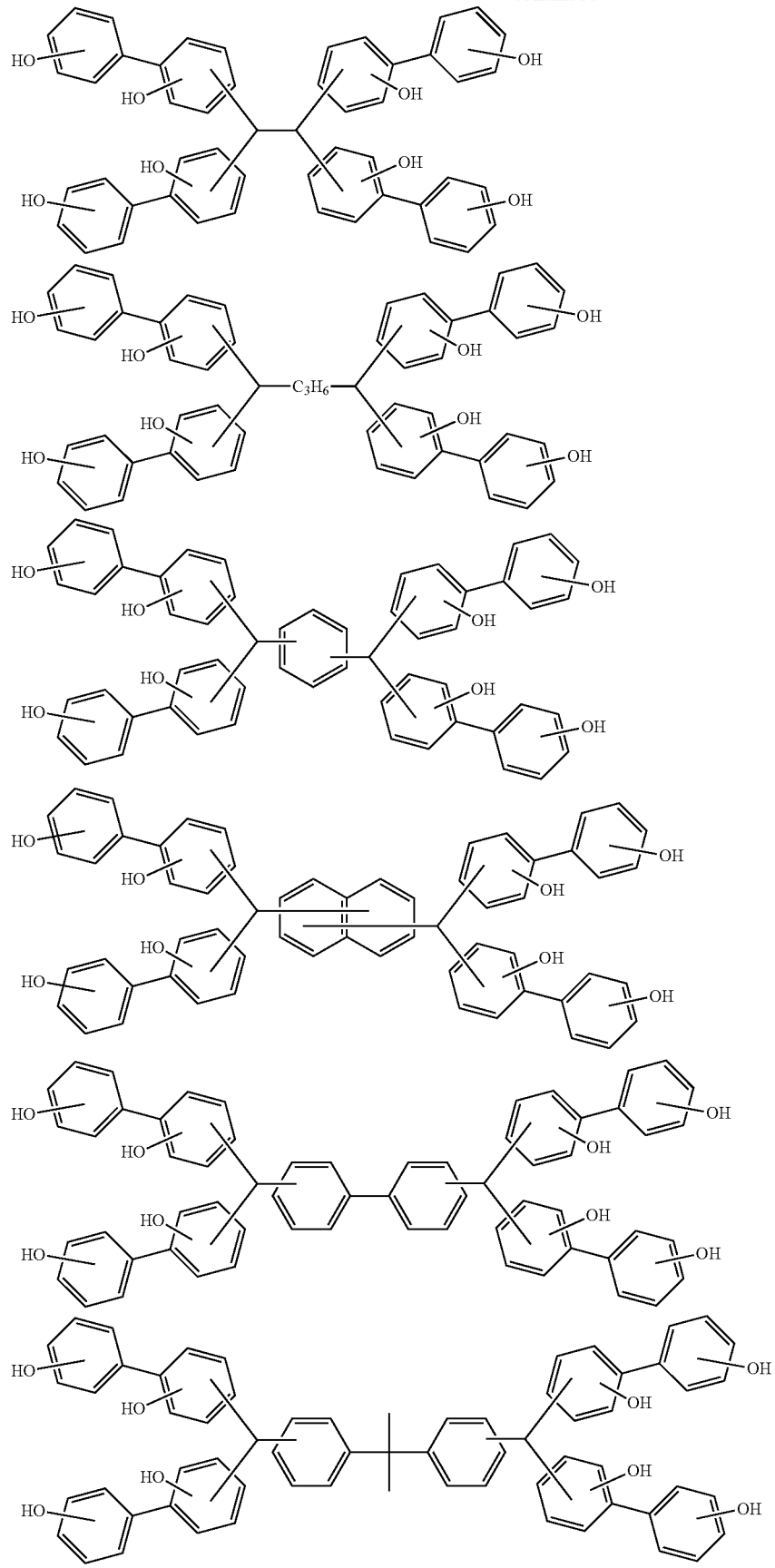

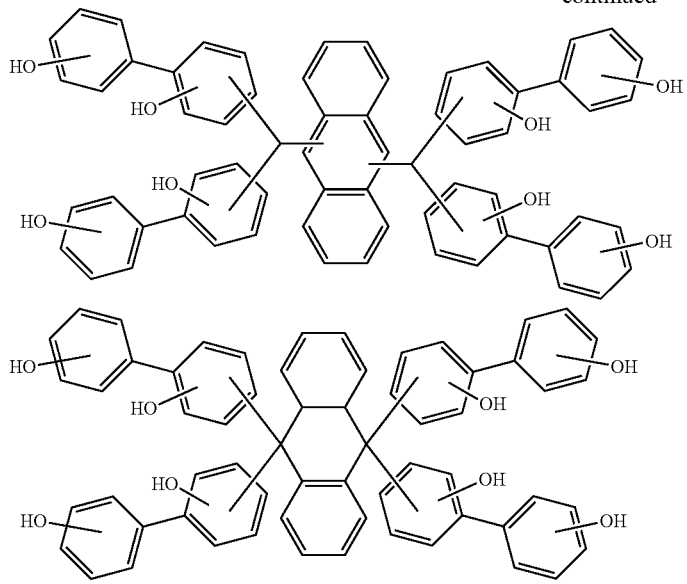

-continued

The compound represented by the formula (1) used in the present embodiment can be arbitrarily synthesized by applying known methods, and the synthesis methods are not particularly limited. The compound represented by the above formula (1) can be obtained, for example, by subjecting a biphenol, a bithiophenol, a binaphthol, a bithionaphthol, or a bianthracenol, and a corresponding aldehyde or ketone to polycondensation reaction in the presence of an acid catalyst at normal pressure. If necessary, this reaction can also be carried out under increased pressure.

Examples of the biphenol include, but not particularly limited to, biphenol, methylbiphenol, and methoxybiphenol. These biphenols may be used alone as one kind or may be used in combination of two or more kinds. Among them, biphenol is preferably used from the viewpoint of the stable supply of raw materials.

Examples of the bithiophenol include, but not particularly limited to, bithiophenol, methylbithiophenol, and methoxybithiophenol. These bithiophenols may be used alone as one kind or may be used in combination of two or more kinds. Among them, bithiophenol is preferably used from the viewpoint of the stable supply of raw materials.

Examples of the binaphthol include, but not particularly limited to, binaphthol, methylbinaphthol, and methoxybinaphthol. These binaphthols may be used alone as one kind or may be used in combination of two or more kinds. Among them, binaphthol is preferably used from the viewpoint of increasing a carbon atom concentration and improving heat resistance.

Examples of the bithionaphthol include, but not particularly limited to, bithionaphthol, methylbithionaphthol, and methoxybithionaphthol. These bithionaphthols may be used alone as one kind or may be used in combination of two or more kinds. Among them, bithionaphthol is preferably used from the viewpoint of increasing a carbon atom concentration and improving heat resistance.

Examples of the bianthracenol include, but not limited to, bianthracenol, methylbianthracenol, and methoxybianthracenol. These bianthracenols may be used alone as one kind or may be used in combination of two or more kinds. Among them, bianthracenol is preferably used from the viewpoint of the stable supply of raw materials.

Examples of the aldehyde include formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane, and benzenetricarboxaldehyde. Benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, or benzenetricarboxaldehyde is preferably used from the viewpoint of providing high heat resistance.

Examples of the ketone include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone. Cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of providing high heat resistance.

The acid catalyst used can be arbitrarily selected from well-known inorganic acids and organic acids. That is, specific examples of the acid catalyst include, but not limited to: inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. From the viewpoint of production such as easy availability and handleability, hydrochloric acid or sulfuric acid is preferably used. As the acid catalyst, one kind or two or more kinds can be used.

Upon the above reaction, a reaction solvent may be used. The reaction solvent is not particularly limited as long as the reaction of the aldehyde or the ketone used with the biphenol, the binaphthol, the bianthracendiol, the bithiophenol, the binaphthalenedithiol, or the bianthracendithiol proceeds. For example, water, methanol, ethanol, propanol, butanol, tetrahydrofuran, dioxane, or a mixed solvent thereof can be used. The amount of the solvent used is not particularly limited and is within the range of, for example, 0 to 2000 parts by mass based on 100 parts by mass of the reaction raw materials. The reaction temperature can be arbitrarily selected according to the reactivity of the reaction raw materials and is usually within the range of 10 to 200° C. For highly selectively synthesizing the compound represented by the formula (1) of the present embodiment, a lower temperature is more preferable. Specifically, the range of 10 to 60° C. is preferable. The method for producing the compound represented by the formula (1) is a method of charging the biphenol, the binaphthol, the bianthracendiol, the bithiophenol, the binaphthalenedithiol, or the bianthracendithiol, the aldehyde or the ketone, and the catalyst at once, or a method of dropping the naphthol, the biphenol, the binaphthol, the bianthracendiol, the bithiophenol, the binaphthalenedithiol, or the bianthracendithiol, and the aldehyde or the ketone in the presence of the catalyst. After the polycondensation reaction terminates, the temperature of the reaction vessel is elevated to 130 to 230° C. in order to remove unreacted raw materials, catalyst, etc. present in the system, and volatile portions can be removed at about 1 to 50 mmHg.

The reaction mentioned above proceeds, for example, but not limited to, by using 2 mol to an excess of the biphenol, the binaphthol, the bianthracendiol, the bithiophenol, the binaphthalenedithiol, or the bianthracendithiol and 0.001 to 1 mol of the acid catalyst, based on 1 mol of the aldehyde or the ketone, and reacting them at 20 to 60° C. at normal pressure for about 20 minutes to 100 hours.

The target component is isolated by a known method after the reaction terminates. An exemplary method involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the objective compound.

Moreover, the resist composition of the present embodiment can form an amorphous film by spin coating. The dissolution rate of the amorphous film formed by spin coating with the resist composition of the present embodiment in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film tends to favorably dissolve in a developing solution, and tends to produce a good resist. When the amorphous film has the dissolution rate of 10000 angstrom/sec or less, the resolution may improve. It is presumed that this is because due to the change in the solubility before and after exposure of the compound represented by the above formula (1), contrast at the interface between the unexposed portion being dissolved in a developing solution and the exposed portion not being dissolved in a developing solution is increased. Moreover, the above dissolution rate is also preferable from the viewpoint of reduction effects of LER and defect.

The dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion tends to be insoluble in a developing solution, and tends to produce a good resist. When the amorphous film has the dissolution rate of 0.0005 angstrom/sec or more, the resolution may improve. It is presumed that this is because the micro surface portion of the compound represented by the above formula (1) dissolves and LER is reduced. Moreover, the above dissolution rate is also preferable from the viewpoint of reduction effects of defect.

The resist composition of the present embodiment preferably further contains a solvent. The resist composition contains preferably 1 to 80% by mass of the solid component and 20 to 99% by mass of the solvent, more preferably 1 to 50% by mass of the solid component and 50 to 99% by mass of the solvent, still more preferably 2 to 40% by mass of the solid component and 60 to 98% by mass of the solvent, and further more preferably 2 to 10% by mass of the solid component and 90 to 98% by mass of the solvent.

The amount of the compound (A) used in the present embodiment is preferably 50 to 99.4% by mass of the total mass of the solid component (summation of optionally used solid component such as compound (A), acid generating agent (C), acid crosslinking agent (G), acid diffusion controlling agent (E), and other component (F), hereinafter the same), more preferably 55 to 90% by mass, still more preferably 60 to 80% by mass, and further preferably 60 to 70% by mass. The above content tends to produce higher resolution, and tends to decrease line edge roughness.

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam. The amount of the acid generating agent (C) used is preferably 0.001 to 49% by mass of the total mass of the solid component, more preferably 1 to 40% by mass, still more preferably 3 to 30% by mass, and further more preferably 10 to 25% by mass. By using it within the above range, a pattern profile with higher sensitivity and low edge roughness tends to be obtained. In the present embodiment, the acid generation method in the system is not particularly limited. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is preferably at least one kind selected from the group consisting of compounds represented by the following formulae (7-1) to (7-8):

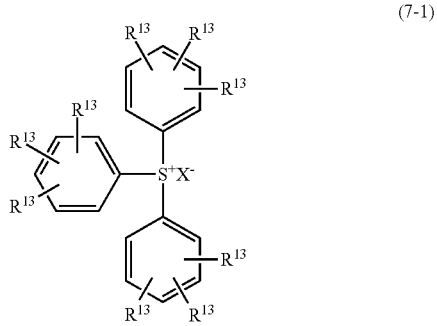
(7-1)

In the formula (7-1), $R^{13}$ may be the same or different, and are each independently a hydrogen atom, a linear, branched or cyclic alkyl group, a linear, branched or cyclic alkoxy group, a hydroxyl group, or a halogen atom; $X^-$ is an alkyl group, an aryl group, a sulfonic acid ion having a halogen substituted alkyl group or a halogen substituted aryl group, or a halide ion.

The compound represented by the above formula (7-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenylsulfonium-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphorsulfonate, diphenyl-4-hydroxyphenylsulfonium 10-camphorsulfonate, and cyclo(1,3-perfluoropropanedisulfone)imidate.

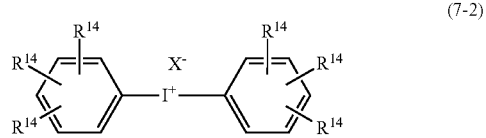
(7-2)

In the formula (7-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as above.

The compound represented by the above formula (7-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

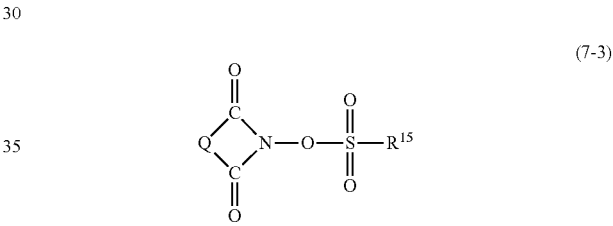
(7-3)

In the formula (7-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (7-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxy)bicyclo[2.2.1]hept-5-en-2,3-dicarboxyimide, N-(2-trifluoromethylbenzenesulfonyloxy)naphthylimide, N-(4-trifluoromethylbenzenesulfonyloxy)bicyclo[2.2.1]hept-5-en-2,3-dicarboxyimide, N-(4-trifluoromethylbenzenesulfonyloxy)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxy)bicyclo[2.2.1]

hept-5-en-2,3-dicarboxyimide, N-(1-naphthalenesulfonyloxy)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

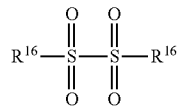

(7-4)

In the formula (7-4), $R^{16}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

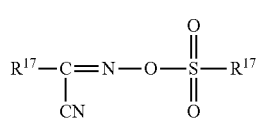

(7-5)

In the formula (7-5), $R^{17}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

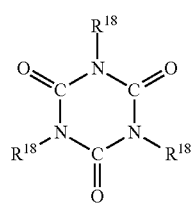

(7-6)

In the formula (7-6), $R^{18}$ may be the same or different, and are each independently a halogenated alkyl group having one or more chlorine atoms and one or more bromine atoms. The number of carbon atoms in the halogenated alkyl group is preferably 1 to 5.

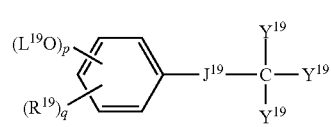

(7-7)

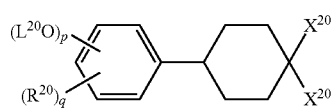

(7-8)

In the above formulae (7-7) and (7-8), $R^{19}$ and $R^{20}$ are each independently an alkyl group having 1 to 3 carbon atoms such as a methyl group, an ethyl group, an n-propyl group, and an isopropyl group; a cycloalkyl group such as a cyclopentyl group and a cyclohexyl group; an alkoxyl group having 1 to 3 carbon atoms such as a methoxy group, an ethoxy group, and a propoxy group; or an aryl group such as a phenyl group, a toluoyl group, and a naphthyl group, and preferably an aryl group having 6 to 10 carbon atoms. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Among these, a 1,2-naphthoquinonediazide-4-sulfonyl group and a 1,2-naphthoquinonediazide-5-sulfonyl group are more preferable. p is an integer of 1 to 3; q is an integer of 0 to 4; and $1 \leq p+q \leq 5$. $J^{19}$ is a single bond, a polymethylene group having 1 to 4 carbon atoms, a cycloalkylene group, a phenylene group, a group represented by the following formula (7-7-1), a carbonyl group, an ester group, an amide group, or an ether group. $Y^{19}$ is a hydrogen atom, an alkyl group, or an aryl group, and $X^{20}$ are each independently a group represented by the following formula (7-8-1):

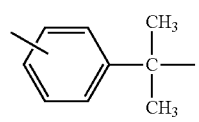

(7-7-1)

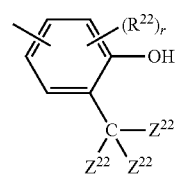

(7-8-1)

In the above formula (7-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.

Examples of the other acid generating agent include, but not limited to, bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis (phenylsulfonylazomethylsulfonyl)butane, 1,6-bis (phenylsulfonylazomethylsulfonyl)hexane, and 1,10-bis (cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the acid generating agents, an acid generating agent having an aromatic ring is preferable, and an acid generating agent represented by the formula (7-1) or (7-2) is more preferable. Among these, an acid generating agent, in which $X^-$ of the formula (7-1) or (7-2) is a sulfonate ion having an aryl group or a halogen-substituted aryl group, is still more preferable; an acid generating agent, in which $X^-$ of the formula (7-1) or (7-2) is a sulfonate ion having an aryl group, is further more preferable; and diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate are yet more preferable. By using the acid generating agent, LER tends to be further reduced.

The acid generating agent (C) can be used alone or in combination of two or more kinds.

The resist composition of the present embodiment preferably contains one or more acid crosslinking agents (G). The acid crosslinking agent (G) is a compound capable of intramolecular or intermolecular crosslinking the compound represented by the formula (1) in the presence of the acid generated from the acid generating agent (C). Examples of such an acid crosslinking agent (G) include a compound having one or more groups (hereinafter, referred to as "crosslinkable group") capable of crosslinking the compound represented by the formula (1).

Specific examples of such a crosslinkable group include, but not limited to, (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group having the acid crosslinking agent (G) of the present embodiment, a hydroxyalkyl group and an alkoxyalkyl group or the like are preferable, and an alkoxymethyl group is more preferable.

Examples of the acid crosslinking agent (G) having the above crosslinkable group include, but not limited to, (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is adjusted to be usually 5 to 100 mol %, preferably 10 to 60 mol %, and more preferably 15 to 40 mol %, based on the total acid functional groups in the compound having a phenolic hydroxyl group, and the alkali soluble resin. Within the above range, the crosslinking reaction tends to sufficiently proceed, and a decrease in the film remaining rate, and swelling phenomena and meandering or the like of a pattern tend to be avoided, which is preferable.

In the resist composition of the present embodiment, as the acid crosslinking agent (G), an alkoxyalkylated urea compound or resin thereof, or an alkoxyalkylated glycoluryl compound or resin thereof is preferable. More preferable examples of the acid crosslinking agent (G) include compounds represented by the following formulae (8-1) to (8-3) and an alkoxymethylated melamine compound (acid crosslinking agent (G1)).

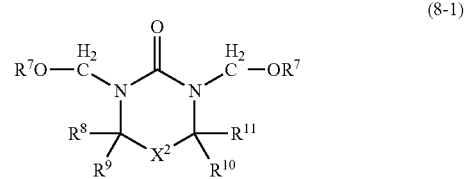

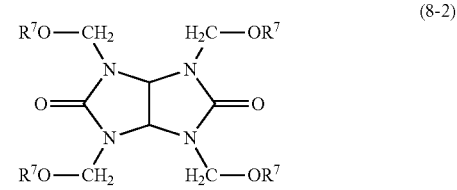

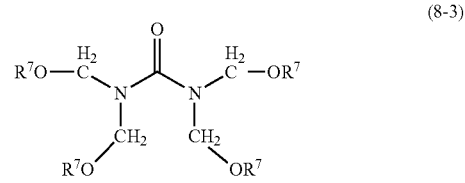

In the above formulae (8-1) to (8-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.

The alkyl group represented by $R^7$ preferably has 1 to 6 carbon atoms, and more preferably 1 to 3 carbon atoms. Examples thereof include a methyl group, an ethyl group, and a propyl group. The acyl group represented by $R^7$ preferably has 2 to 6 carbon atoms, and more preferably 2 to 4 carbon atoms. Examples thereof include an acetyl group and a propionyl group. The alkyl group represented by $R^8$ to $R^{11}$ preferably has 1 to 6 carbon atoms, and more preferably 1 to 3 carbon atoms. Examples thereof include a methyl group, an ethyl group, and a propyl group. The alkoxy group represented by $R^8$ to $R^{11}$ preferably has 1 to 6 carbon atoms, and more preferably 1 to 3 carbon atoms. Examples thereof include a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different. Specific examples of the compound represented by the formula (8-1) include compounds shown below:

Specific examples of the compound represented by the formula (8-1) include, but not limited to, compounds represented below:

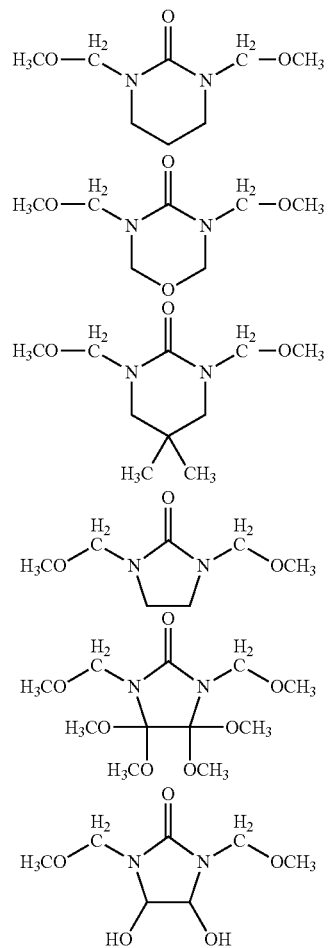

Specific examples of the compound represented by the formula (8-2) include, but not limited to, N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among these, N,N,N,N-tetra(methoxymethyl)glycoluryl is preferable.

Specific examples of the compound represented by the formula (8-3) include, but not limited to, compounds represented below:

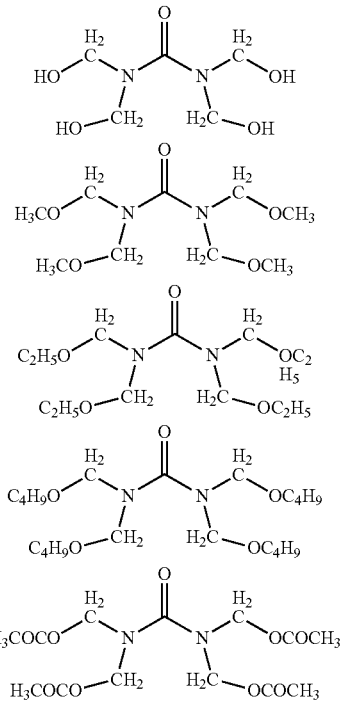

Specific examples of the alkoxymethylated melamine compound include, but not limited to, N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among these, N,N,N,N,N,N-hexa(methoxymethyl)melamine is preferable.

The above acid crosslinking agent (G1) can be obtained by, for example, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by MT AquaPolymer) and NIKALAC (manufactured by Sanwa Chemical).

Other preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). More preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of the above benzene rings, or a plurality of benzene rings.

The hydroxyalkyl group bonded to a benzene ring is the one having 1 to 6 carbon atoms such as a hydroxymethyl group, a 2-hydroxyethyl group, and a 2-hydroxy-1-propyl group is preferable. As the alkoxyalkyl group bonded to a benzene ring, the one having 2 to 6 carbon atoms is preferable. Specifically, a methoxymethyl group, an ethoxymethyl group, an n-propoxymethyl group, an iso-propoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:

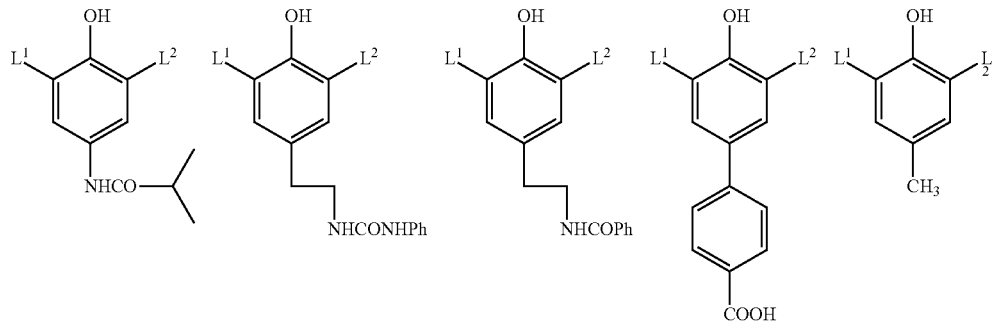

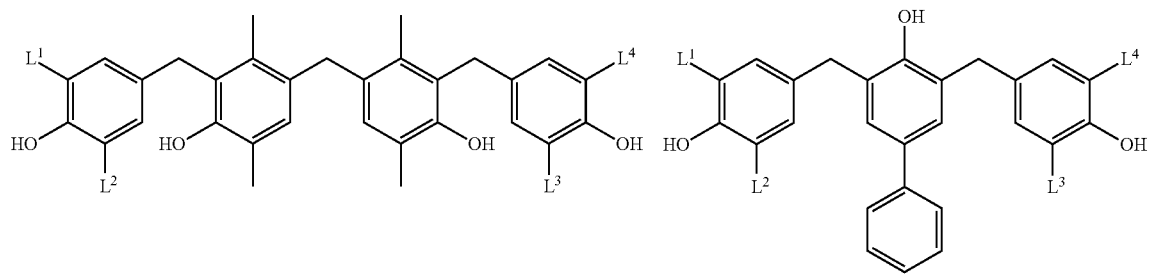

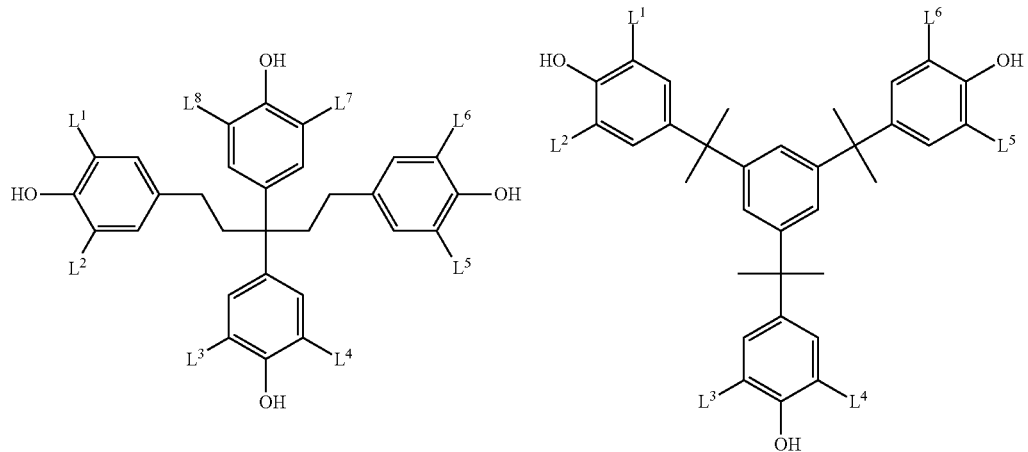

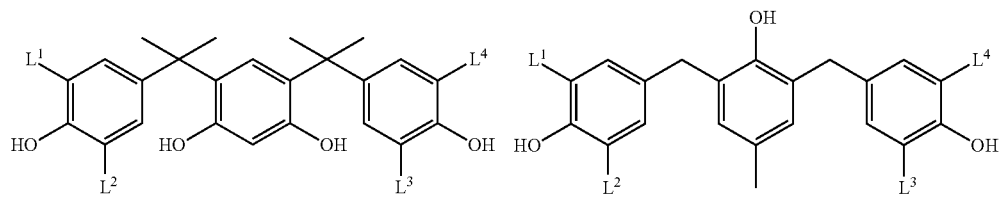

-continued
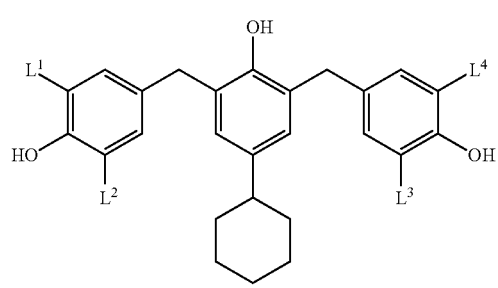
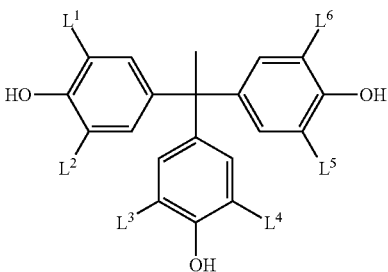
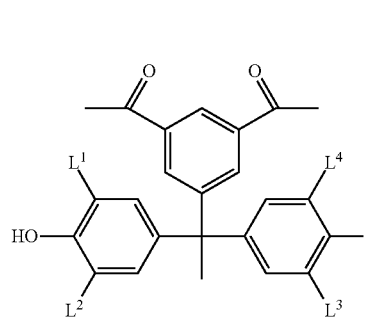
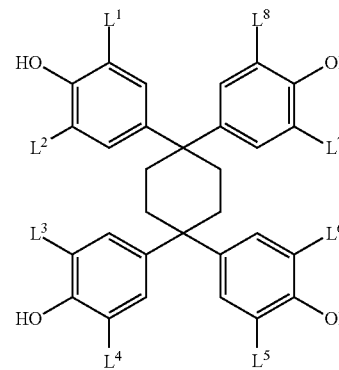
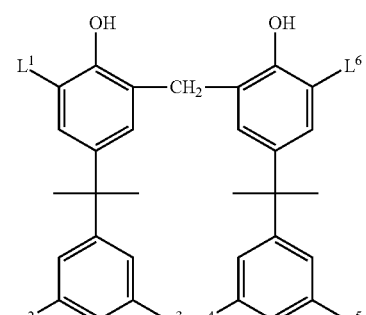
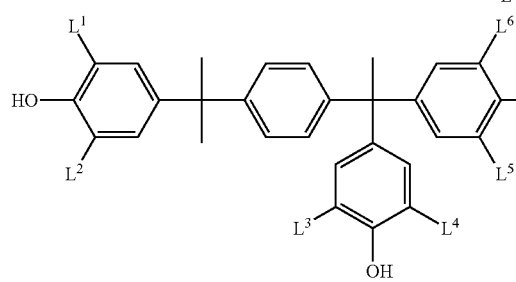
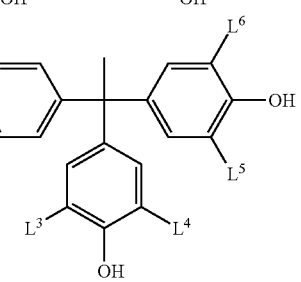
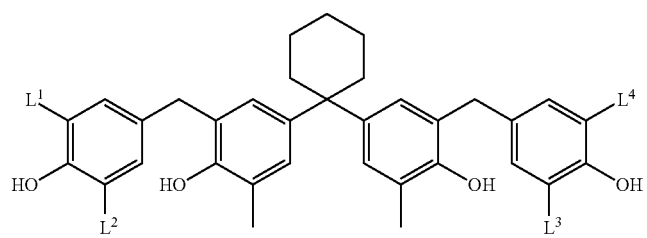
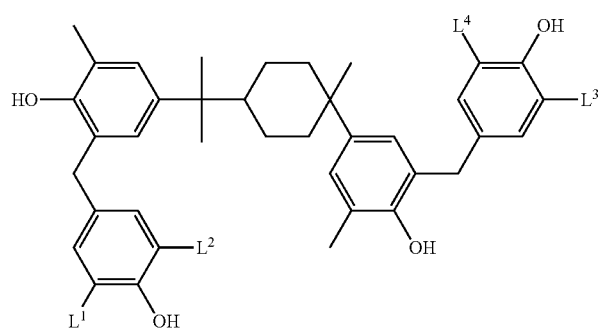
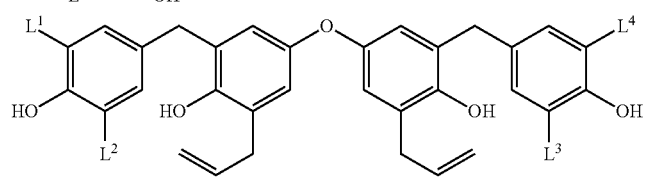

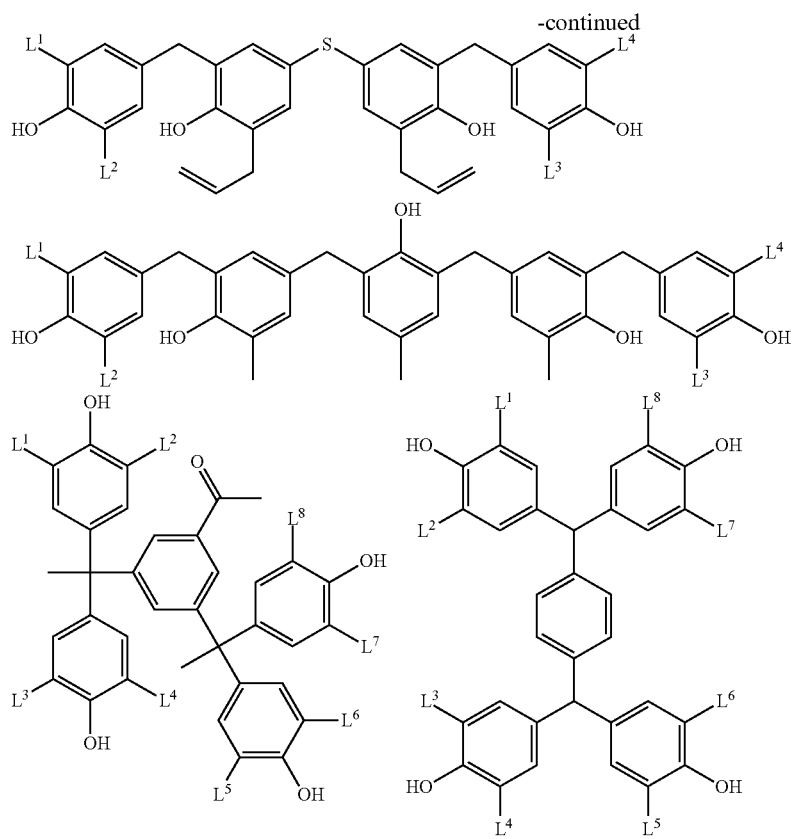

In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the above formulae are a hydrogen atom) with formaldehyde in the presence of a basic catalyst. In this case, in order to prevent resinification and gelation, the reaction temperature is preferably 60° C. or less. Specifically, it can be synthesized by methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, in order to prevent resinification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation groups (R—COO— group, R—SO$_2$— group or the like, wherein R represents a substituent group selected from the group consisting of a linear hydrocarbon group having 1 to 12 carbon atoms, a cyclic hydrocarbon group having 3 to 12 carbon atoms, an alkoxy group having 1 to 12 carbon atoms, a 1-branched alkyl group having 3 to 12 carbon atoms, and an aromatic hydrocarbon group having 6 to 12 carbon atoms). Examples of a compound having the above α-hydroxyisopropyl group include, but not limited to, one kind or two kinds or more of a substituted or non-substituted aromatic based compound, a diphenyl compound, a naphthalene compound, a furan compound or the like containing at least one α-hydroxyisopropyl group. Specific examples thereof include a compound represented by the following formula (9-1) (hereinafter, referred to as "benzene based compound (1)"), a compound represented by the following formula (9-2) (hereinafter, referred to as "diphenyl based compound (2)"), a compound represented by the following formula (9-3) (hereinafter, referred to as "naphthalene based compound (3)"), and a compound represented by the following formula (9-4) (hereinafter, referred to as "furan based compound (4)").

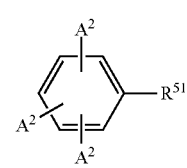

(9-1)

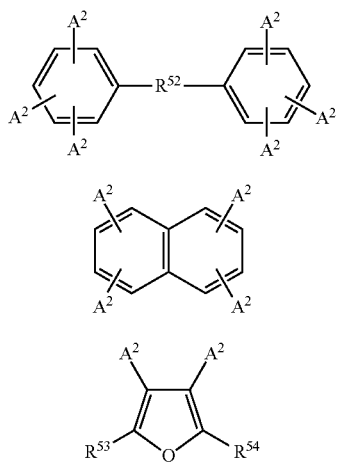

(9-2)

(9-3)

(9-4)

In the above formulae (9-1) to (9-4), each $A^2$ independently represents an α-hydroxyisopropyl group or a hydrogen atom, and at least one $A^2$ is an α-hydroxyisopropyl group. In the formula (9-1), $R^{51}$ represents a hydrogen atom, a hydroxyl group, a linear or branched alkylcarbonyl group having 2 to 6 carbon atoms, or a linear or branched alkoxycarbonyl group having 2 to 6 carbon atoms. Furthermore, in the formula (9-2), $R^{52}$ represents a single bond, a linear or branched alkylene group having 1 to 5 carbon atoms, —O—, —CO—, or —COO—. Also, in the formula (9-4), $R^{53}$ and $R^{54}$ represent a hydrogen atom or a linear or branched alkyl group having 1 to 6 carbon atoms independently from each other.

Specific examples of the benzene based compound (1) include, but not limited to, α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl-n-propyl ketone, 4-α-hydroxyisopropylphenyl isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) include, but not limited to, α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl) biphenyl; α-hydroxyisopropyldiphenylalkanes such as 3-α-hydroxyisopropyldiphenylmethane, 4-α-hydroxyisopropyldiphenylmethane, 1-(4-α-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane; α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether; α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl) diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl) benzoate, 3-α-hydroxyisopropylphenyl 3-α-hydroxyisopropylbenzoate, 4-α-hydroxyisopropylphenyl 3-α- hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) include, but not limited to, 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the above furan based compound (4) include, but not limited to, 3-(α-hydroxyisopropyl) furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are more preferable; and α-hydroxyisopropylbiphenyls having two or more α-hydroxyisopropyl groups and the above naphthalene based compound (3) having two or more α-hydroxyisopropyl groups are still more preferable.

The above acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

The amount of the acid crosslinking agent (G) used in the present embodiment is preferably 0.5 to 49% by mass of the total mass of the solid component, more preferably 0.5 to 40% by mass, still more preferably 1 to 30% by mass, and further more preferably 2 to 20% by mass. When the content of the above acid crosslinking agent (G) is 0.5% by mass or more, the inhibiting effect of the solubility of a resist film in an alkaline developing solution tends to be improved, and a decrease in the film remaining rate, and occurrence of swelling and meandering of a pattern tends to be able to be inhibited, which is preferable. On the other hand, when the content is 50% by mass or less, a decrease in heat resistance as a resist tends to be able to be inhibited, which is preferable.

The content of at least one kind of compound selected from the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

In all acid crosslinking agent components, the content of the alkoxymethylated melamine compound and/or the compounds represented by formula (9-1) to formula (9-3) is preferably 50 to 99% by mass, more preferably 60 to 99% by mass, much more preferably 70 to 98% by mass, and further more preferably 80 to 97% by mass. By having the alkoxymethylated melamine compound and/or the compounds represented by formula (9-1) to formula (9-3) of 50% by mass or more of all acid crosslinking agent components, the resolution tends to be further improved, which is preferable. By having the compounds of 99% by mass or less, the pattern cross section tends to be likely to have a rectangular shape, which is preferable.

In the present embodiment, the resist composition may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition tends to be improved. Also, along with the further improvement of the resolution, the line width change of a resist pattern due to variation in the post exposure delay time before radiation irradiation and the post exposure delay time after radiation irradiation can be inhibited, and the composition tends to have extremely excellent process stability. Such an acid diffusion controlling agent (E) includes a radiation degradable basic compound such as a nitrogen atom-containing basic compound, a basic sulfonium compound, and a basic iodonium compound. The acid diffusion controlling agent (E) can be used alone or in combination of two or more kinds.

Examples of the above acid diffusion controlling agent include, but not limited to, a nitrogen-containing organic compound, and a basic compound degradable by exposure. Examples of the above nitrogen-containing organic compound include, but not limited to, a compound represented by the following formula (10):

(10)

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above formula (10), $R^{61}$, $R^{62}$, and $R^{63}$ represent a hydrogen atom, a linear, branched or cyclic alkyl group, an aryl group, or an aralkyl group independently from each other. The above alkyl group, aryl group, or aralkyl group may be non-substituted or may be substituted with a hydroxyl group or the like. Herein, examples of the above linear, branched or cyclic alkyl group include the one having 1 to 15 carbon atoms, and preferably 1 to 10 carbon atoms. Specific examples thereof include a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the above aryl group include the one having 6 to 12 carbon atoms. Specific examples thereof include a phenyl group, a tolyl group, a xylyl group, a cumenyl group, and a 1-naphthyl group. Furthermore, examples of the above aralkyl group include the one having 7 to 19 carbon atoms, and preferably 7 to 13 carbon atoms. Specific examples thereof include a benzyl group, an α-methylbenzyl group, a phenethyl group, and a naphthylmethyl group.

Specific examples of the above nitrogen-containing compound (I) include, but not limited to, mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the above nitrogen-containing compound (II) include, but not limited to, ethylenediamine, N,N,N',N'-tetramethylethylenediamine, N,N,N',N'-tetrakis (2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the above nitrogen-containing compound (III) include, but not limited to, polymers of polyethyleneimine, polyarylamine, and N-(2-dimethylaminoethyl)acrylamide.

Specific examples of the above amide group-containing compound include, but not limited to, formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the above urea compound include, but not limited to, urea, methylurea, 1,1-dimethylurea, 1,3-dimethylurea, 1,1,3,3-tetramethylurea, 1,3-diphenylurea, and tri-n-butylthiourea.

Specific examples of the above nitrogen-containing heterocyclic compound include, but not limited to, imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the radiation degradable basic compound can include a sulfonium compound represented by the following formula (11-1), and an iodonium compound represented by the following formula (11-2):

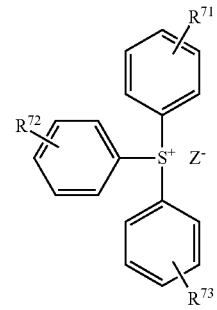

(11-1)

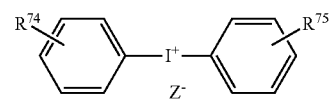

(11-2)

In the above formulae (11-1) and (11-2), $R^{71}$, $R^{72}$, $R^{73}$, $R^{74}$, and $R^{75}$ represent a hydrogen atom, an alkyl group having 1 to 6 carbon atoms, an alkoxyl group having 1 to 6 carbon atoms, a hydroxyl group, or a halogen atom independently from each other. $Z^-$ represents $HO^-$, R—COO⁻ (R represents an alkyl group having 1 to 6 carbon atoms, an aryl group having 6 to 11 carbon atoms, or an alkaryl group having 7 to 12 carbon atoms), or an anion represented by the following formula (11-3):

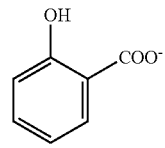

(11-3)

Specific examples of the above radiation degradable basic compound include, but not limited to, triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) is preferably 0.001 to 49% by mass of the total mass of the solid component, more preferably 0.01 to 10% by mass, still more preferably 0.01 to 5% by mass, and further more preferably 0.01 to 3% by mass. Within the above range, a decrease in resolution, and deterioration of the pattern shape and the dimension fidelity or the like tend to be prevented. Moreover, even though the post exposure delay time from electron beam irradiation to heating after radiation irradiation becomes longer, deterioration in the shape of the pattern upper layer portion tends to be inhibited. When the content is 10% by mass or less, a decrease in sensitivity, and developability of the unexposed portion or the like tends to be able to be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition tends to be extremely excellent process stability.

To the resist composition of the present embodiment, within the range of not inhibiting the purpose of the present embodiment, if required, as the other component (F), one kind or two kinds or more of various additive agents such as a dissolution promoting agent, a dissolution controlling agent, a sensitizing agent, a surfactant and an organic carboxylic acid or an oxo acid of phosphor, or derivative thereof can be added.

[Dissolution Promoting Agent]

A dissolution promoting agent is a component having a function of increasing the solubility of a compound represented by the formula (1) in a developing solution to moderately increase the dissolution rate of the compound upon developing, when the solubility of the compound is too low. The low molecular weight dissolution promoting agent can be used, within the range of not deteriorating the effect of the present embodiment. Examples of the above dissolution promoting agent include a low molecular weight phenolic compound. Specific examples thereof include bisphenols and tris(hydroxyphenyl)methane. These dissolution promoting agents can be used alone or in mixture of two or more kinds. The content of the dissolution promoting agent, which is arbitrarily adjusted according to the kind of the compound to be used, is preferably 0 to 49% by mass of the total mass of the solid component, more preferably 0 to 5% by mass, still more preferably 0 to 1% by mass, and further more preferably 0% by mass.

[Dissolution Controlling Agent]

The dissolution controlling agent is a component having a function of controlling the solubility of the compound represented by the formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable. Examples of the dissolution controlling agent include, but not limited to, aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent is arbitrarily adjusted according to the kind of the compound to be used, is preferably 0 to 49% by mass of the total mass of the solid component, more preferably 0 to 5% by mass, still more preferably 0 to 1% by mass, and further more preferably 0% by mass.

[Sensitizing Agent]

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include benzophenones, biacetyls, pyrenes, phenothiazines, and fluorenes. These sensitizing agents can be used alone or in two or more kinds. The content of the sensitizing agent, which is arbitrarily adjusted according to the kind of the compound to be used, is preferably 0 to 49% by mass of the total mass of the solid component, more preferably 0 to 5% by mass, still more preferably 0 to 1% by mass, and further more preferably 0% by mass.

[Surfactant]

The surfactant is a component having a function of improving coatability and striation of the resist composition of the present embodiment, and developability of a resist or the like. Such a surfactant may be any of anionic, cationic, nonionic or amphoteric. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.). The content of the surfactant is arbitrarily adjusted according to the kind of the compound to be used, is preferably 0 to 49% by mass of the total mass of the solid component, more preferably 0 to 5% by mass, still more preferably 0 to 1% by mass, and further more preferably 0% by mass.

[Organic Carboxylic Acid, or Oxo Acid of Phosphor or Derivative Thereof]

For the purpose of prevention of sensitivity deterioration or improvement of a resist pattern shape and post exposure delay stability or the like, and as an additional optional component, an organic carboxylic acid or an oxo acid of phosphor or derivative thereof may be contained. The composition can be used in combination with the acid diffusion controlling agent, or may be used alone. As the organic carboxylic acid, not particularly limited, for example, malonic acid, citric acid, malic acid, succinic acid, benzoic acid, and salicylic acid, or the like are preferable. Examples of the oxo acid of phosphor or derivative thereof include, but not limited to, phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound to be used, is preferably 0 to 49% by mass of the total mass of the solid component, more preferably 0 to 5% by mass, still more preferably 0 to 1% by mass, and further more preferably 0% by mass.

[Other Additive Agent Excluding Additives Mentioned Above (Dissolution Promoting Agent, Dissolution Controlling Agent, Sensitizing Agent, Surfactant and Organic Carboxylic Acid or Oxo Acid of Phosphor, or Derivative Thereof, Etc.)]

Furthermore, the resist composition of the present embodiment can contain one kind or two kinds or more of additive agents other than the above dissolution controlling agent, sensitizing agent, and surfactant, within the range of not inhibiting the purpose of the present embodiment, if required. Examples of such an additive agent include, but not limited to, a dye, a pigment, and an adhesion aid. For example, the composition contains the dye or the pigment, and thereby a latent image of the exposed portion can be visualized and influence of halation upon exposure tends to be alleviated, which is preferable. The composition contains the adhesion aid, and thereby adhesiveness to a substrate tends to be improved, which is preferable. Furthermore, examples of other additive agent include a halation preventing agent, a storage stabilizing agent, a defoaming agent, and a shape improving agent. Specific examples thereof include 4-hydroxy-4'-methylchalkone.

The total amount of the optional component (F) is preferably 0 to 49% by mass of the total mass of the solid component, more preferably 0 to 5% by mass, still more preferably 0 to 1% by mass, and further more preferably 0% by mass.

The content of the resist composition of the present embodiment (the compound (A)/the acid generating agent (C)/the acid crosslinking agent (G)/the acid diffusion controlling agent (E)/the optional component (F)) is preferably 50 to 99.4/0.001 to 49/0.5 to 49/0.001 to 49/0 to 49 in % by mass based on the solid content, more preferably 55 to 90/1 to 40/0.5 to 40/0.01 to 10/0 to 5, still more preferably 60 to 80/3 to 30/1 to 30/0.01 to 5/0 to 1, and further more preferably 60 to 70/10 to 25/2 to 20/0.01 to 3/0. The content ratio of each component is selected from each range so that the summation thereof is 100% by mass. By the above content ratio, performance such as sensitivity, resolution, and developability tends to be excellent.

The resist composition of the present embodiment is usually prepared by dissolving each component in a solvent upon use into a homogenous solution, and then if required, filtering through a filter or the like with a pore diameter of about 0.2 µm, for example.

Examples of the solvent used in the preparation of the resist composition of the present embodiment can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as α-lactone. These solvents can be used alone or in combination of two or more kinds.

The resist composition of the present embodiment can contain a resin within the range of not inhibiting the purpose of the present embodiment. Examples of the resin include a novolac resin, polyvinyl phenols, polyacrylic acid, polyvinyl alcohol, a styrene-maleic anhydride resin, an acrylic acid, vinyl alcohol or vinylphenol as a monomeric unit, or derivative thereof. The content of the resin is arbitrarily adjusted according to the kind of the compound represented by the formula (1) to be used, is preferably 30 parts by mass or less per 100 parts by mass of the compound, more preferably 10 parts by mass or less, still more preferably 5 parts by mass or less, and further more preferably 0 part by mass.

[Resist Pattern Formation Method]

A resist pattern formation method according to the present embodiment includes steps of forming a resist film by coating a substrate with the above resist composition of the present embodiment, exposing the formed resist film, and developing the exposed resist film. The resist pattern formed by the resist pattern formation method according to the present embodiment is excellent in its shape. The resist pattern according to the present embodiment can also be formed as an upper layer resist in a multilayer process.

In order to form a resist pattern, a resist film is formed by coating a conventionally known substrate with the resist composition of the present embodiment using a coating means such as spin coating, flow casting coating, and roll coating. The conventionally known substrate is not particularly limited. For example, a substrate for electronic components, and the one having a predetermined wiring pattern formed thereon, or the like can be exemplified. More specific examples include a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic and/or organic film provided thereon. Examples of the inorganic film include, but not particularly limited to, an inorganic antireflection film (inorganic BARC). Examples of the organic film include, but not particularly limited to, an organic antireflection film (organic BARC). Surface treatment with hexamethylene disilazane or the like may be conducted.

Next, the coated substrate is heated if required. The heating conditions vary according to the content composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation. The heating conditions vary according to the compounding composition of the resist composition, or the like, but are preferably 20 to 250° C., and more preferably 20 to 150° C.

Next, by developing the exposed resist film in a developing solution, a predetermined resist pattern is formed. As the developing solution, a solvent having a solubility parameter (SP value) close to that of the compound of the formula (1) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include, but not limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include, but not limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include, but not limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monomethyl ether, and methoxymethyl butanol.

Examples of the ether-based solvent include, but not limited to, dioxane and tetrahydrofuran in addition to the above glycol ether-based solvents.

Examples of the amide-based solvent which can be used include, but not limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not limited to, an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the desired effect of the present embodiment, the water content ratio as the whole developing solution is preferably less than 70% by mass, more preferably less than 50% by mass, still more preferably less than 30% by mass, and further preferably less than 10% by mass. Still further preferably, the developing solution is substantially moisture free. That is, the content of the organic solvent in the developing solution is preferably 30% by mass or more and 100% by mass or less based on the total amount of the developing solution, more preferably 50% by mass or more and 100% by mass or less, still more preferably 70% by mass or more and 100% by mass or less, further more preferably 90% by mass or more and 100% by mass or less, and yet more preferably 95% by mass or more and 100% by mass or less.

Examples of the alkaline aqueous solution include, but not limited to, an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent tends to improve resist performance such as resolution and roughness of the resist pattern, which is preferable.

The vapor pressure of the developing solution is preferably 5 kPa or less at 20° C., more preferably 3 kPa or less, and still more preferably 2 kPa or less. The evaporation of the developing solution on the substrate or in a developing cup tends to be inhibited by setting the vapor pressure of the developing solution to 5 kPa or less, to improve temperature uniformity within a wafer surface, thereby resulting in a tendency of improvement in size uniformity within the wafer surface.

Specific examples of developing solution having a vapor pressure of 5 kPa or less include, but not limited to, a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples of developing solution having a vapor pressure of 2 kPa or less which is a particularly preferable range include, but not limited to, a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is more preferably used.

The amount of the surfactant used is usually 0.001 to 5% by mass based on the total amount of the developing solution, preferably 0.005 to 2% by mass, and more preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be carried out.

A step of rinsing the resist film with a rinsing solution containing an organic solvent is preferably carried out after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Further more preferably, after development, a step of rinsing the film by using a rinsing solution containing a monohydric alcohol is conducted. Yet more preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development include a linear, branched or cyclic monohydric alcohol. Specific examples include, but not limited to, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like can be used. Examples of monohydric alcohol having 5 or more carbon atoms include, but not limited to, 1-hexanol, 2-hexanol, 4-methyl-2-pentanol, 1-pentanol, and 3-methyl-1-butanol or the like can be used.

A plurality of these components may be mixed, or the component may be used by mixing the component with an organic solvent other than those described above.

The water content ratio in the rinsing solution is preferably 10% by mass or less, more preferably 5% by mass or less, and still more preferably 3% by mass or less. By setting the water content ratio to 10% by mass or less, better development characteristics tend to be obtained.

The vapor pressure at 20° C. of the rinsing solution used after development is preferably 0.05 kPa or more and 5 kPa or less, more preferably 0.1 kPa or more and 5 kPa or less, and much more preferably 0.12 kPa or more and 3 kPa or less. By setting the vapor pressure of the rinsing solution to 0.05 kPa or more and 5 kPa or less, the temperature uniformity in the wafer surface tends to be enhanced and moreover, swelling due to permeation of the rinsing solution is further inhibited. As a result, the dimensional uniformity in the wafer surface tends to be further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a known method such as dry etching using plasma gas, and wet etching with an alkaline solution, a cupric chloride solution, and a ferric chloride solution or the like.

After forming the resist pattern, plating can also be conducted. Examples of the above plating method include, but not limited to, copper plating, solder plating, nickel plating, and gold plating.

The remaining resist pattern after etching can be peeled by an organic solvent. Examples of the above organic solvent include PGMEA (propylene glycol monomethyl ether acetate), PGME (propylene glycol monomethyl ether), and EL (ethyl lactate). Examples of the above peeling method include a dipping method and a spraying method. A wiring substrate having a resist pattern formed thereon may be a multilayer wiring substrate, and may have a small diameter through hole.

The wiring substrate obtained in the present embodiment can also be formed by a method for forming a resist pattern, then depositing a metal in vacuum, and subsequently dissolving the resist pattern in a solution, i.e., a liftoff method.

EXAMPLES

The present embodiment will be more specifically described with reference to examples below. However, the present embodiment is not limited to these examples. Hereinafter, the structure of a compound in examples and comparative examples was confirmed by $^1$H-NMR measurement.
(Carbon Concentration and Oxygen Concentration)
A carbon concentration and an oxygen concentration (% by mass) were measured by organic elemental analysis.
Apparatus: CHN Corder MT-6 (manufactured by Yanaco Analytical Instruments Inc.)
(Molecular Weight)
A molecular weight was measured using Acquity UPLC/MALDI-Synapt HDMS manufactured by Water Corporation according to LC-MS analysis.
(Solubility)
The dissolution amount of the compound in 1-methoxy-2-propanol (PGME) and propylene glycol monomethyl ether acetate (PGMEA) was measured at 23° C., and the results were evaluated according to the following standard.
Evaluation A: 20% by weight or more
Evaluation B: 10% by weigh or more and less than 20% by weight
Evaluation C: less than 10% by weight (Synthesis Example 1) Synthesis of BiF-1

A container (internal capacity: 200 mL) equipped with a stirrer, a condenser tube, and a burette was prepared. In this container, 30 g (161 mmol) of 4,4-biphenol (reagent manufactured by Tokyo Kasei Kogyo Co., Ltd.), 15 g (82 mmol) of 4-biphenylaldehyde (manufactured by Mitsubishi Gas Chemical Company, Inc.), and 100 mL of butyl acetate were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 5.8 g of the objective compound represented by the following formula (BiF-1).

The following peaks were found by 400 MHz-$^1$H-NMR, and the compound was confirmed to have a chemical structure of the following formula.
$^1$H-NMR: (d-DMSO, internal standard TMS)
δ (ppm) 9.4 (4H, O—H), 6.8 to 7.8 (22H, Ph-H), 6.2 (1H, C—H)

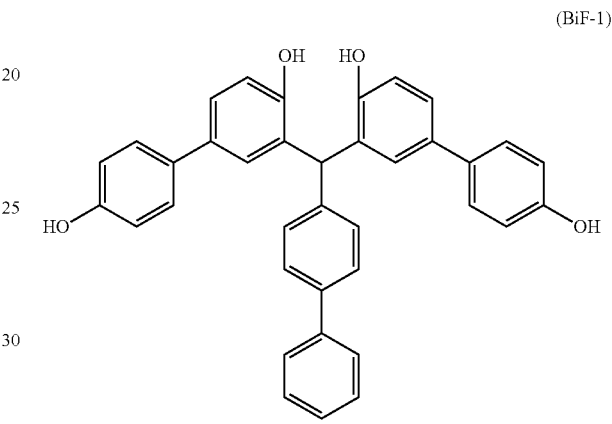

(BiF-1)

As a result of organic elemental analysis, the obtained compound (BiF-1) had a carbon concentration of 82.9% and an oxygen concentration of 11.8%. Because of the high carbon content and the low oxygen content, the compound (BiF-1) was evaluated as having high etching resistance.

As a result of measuring the molecular weight of the obtained compound by the above method, the molecular weight was determined to be 536.

As a result of thermogravimetry (TG), the 10% thermal reduction temperature of the obtained compound (BiF-1) was determined to be 400° C. or higher. Therefore, this compound was evaluated as having high heat resistance and being applicable to baking at a high temperature.

As a result of evaluating solubility in PGME and PGMEA, it was determined to be 30 wt % or more (evaluation A), and the compound (BiF-1) was evaluated as having excellent solubility. Therefore, the compound (BiF-1) was evaluated as having high storage stability in a solution state and being sufficiently applicable to even an edge bead rinse liquid (PGME/PGMEA mixed solution) widely used in the finer processing of semiconductors.

(Synthesis Example 2) Synthesis of BiF-2

A container (internal capacity: 300 mL) equipped with a stirrer, a condenser tube, and a burette was prepared. In this container, 60 g (178 mmol) of OPP-BP (manufactured by Honshu Chemical Industry Co., Ltd.), 16 g (89 mmol) of 4-biphenylaldehyde (manufactured by Mitsubishi Gas Chemical Company, Inc.), and 100 mL of butyl acetate were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 5 hours to perform reaction. Next, the reaction solution was concentrated. The reaction product was precipitated by the addition of 100 g of heptane. After cooling to room temperature, the precipitates were separated by filtration. The solid matter obtained by filtration was dried, and then separated and purified by column chromatography to obtain 7.5 g of the objective compound (BiF-2) represented by the following formula.

The following peaks were found by 400 MHz-$^1$H-NMR, and the compound was confirmed to have a chemical structure of the following formula.

$^1$H-NMR: (d-DMSO, internal standard TMS)
δ (ppm) 9.1 (4H, O—H), 6.8 to 8.2 (39H, Ph-H), 6.5 (1H, C—H)

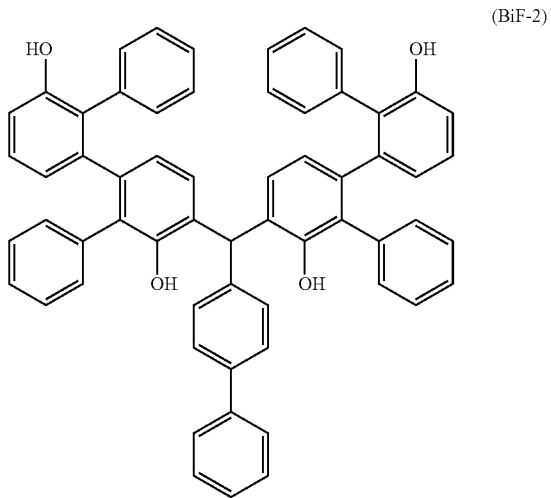 [SMILES: Oc1cccc(-c2ccc(C(c3ccc(-c4ccccc4)cc3)c3ccc(-c4cccc(O)c4-c4ccccc4)c(-c4ccccc4)c3O)c(O)c2-c2ccccc2)c1-c1ccccc1]

(BiF-2)

As a result of organic elemental analysis, the obtained compound (BiF-2) had a carbon concentration of 87.1% and an oxygen concentration of 7.6%. Because of the high carbon content and the low oxygen content, the compound (BiF-2) was evaluated as having high etching resistance.

As a result of measuring the molecular weight of the obtained compound by the above method, the molecular weight was determined to be 840.

As a result of thermogravimetry (TG), the 10% thermal reduction temperature of the obtained compound (BiF-2) was determined to be 400° C. or higher. Therefore, this compound was evaluated as having high heat resistance and being applicable to baking at a high temperature.

As a result of evaluating solubility in PGME and PGMEA, it was determined to be 30 wt % or more (evaluation A), and the compound (BiF-2) was evaluated as having excellent solubility. Therefore, the compound (BiF-2) was evaluated as having high storage stability in a solution state and being sufficiently applicable to even an edge bead rinse liquid (PGME/PGMEA mixed solution) widely used in the finer processing of semiconductors.

As a result of organic elemental analysis, the obtained compound (BiF-1) had a carbon concentration of 82.9% and an oxygen concentration of 11.8%. Because of the high carbon content and the low oxygen content, the compound (BiF-1) was evaluated as having high etching resistance.

As a result of measuring the molecular weight of the obtained compound by the above method, the molecular weight was determined to be 536.

(Synthesis Example 3) Synthesis of TeF-1

A container (internal capacity: 500 mL) equipped with a stirrer, a condenser tube, and a burette was prepared. In this container, 30 g (161 mmol) of 4,4-biphenol (reagent manufactured by Tokyo Kasei Kogyo Co., Ltd.), 8.5 g (40 mmol) of 4,4'-biphenyldicarboxaldehyde (reagent manufactured by Tokyo Kasei Kogyo Co., Ltd.), and 300 g of Ethylglyme (special grade reagent manufactured by Tokyo Kasei Kogyo Co., Ltd.) were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 4.0 g of the objective compound (TeF-1) represented by the following formula.

The following peaks were found by 400 MHz-$^1$H-NMR, and the compound was confirmed to have a chemical structure of the following formula.

$^1$H-NMR: (d-DMSO, internal standard TMS)
δ (ppm) 9.4 (8H, O—H), 6.8 to 7.8 (36H, Ph-H), 6.2 (2H, C—H)

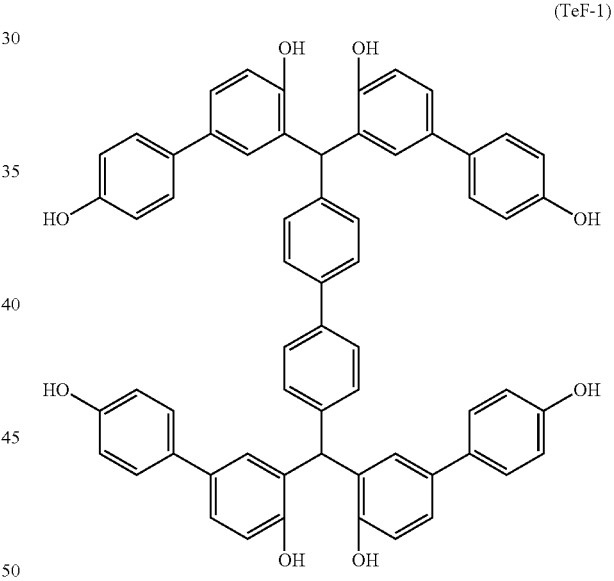

(TeF-1)

As a result of organic elemental analysis, the obtained compound (TeF-1) had a carbon concentration of 81.03% and an oxygen concentration of 13.93%. Because of the high carbon content and the low oxygen content, the compound (TeF-1) was evaluated as having high etching resistance.

As a result of measuring the molecular weight of the obtained compound by the above method, the molecular weight was determined to be 918.

As a result of thermogravimetry (TG), the 10% thermal reduction temperature of the obtained compound (TeF-1) was determined to be 400° C. or higher. Therefore, this compound was evaluated as having high heat resistance and being applicable to baking at a high temperature.

As a result of evaluating solubility in PGME and PGMEA, it was determined to be 30 wt % or more (evaluation A), and the compound (TeF-1) was evaluated as having excellent solubility. Therefore, the compound (TeF-1) was evaluated as having high storage stability in a solution state and being sufficiently applicable to even an edge bead rinse liquid (PGME/PGMEA mixed solution) widely used in the finer processing of semiconductors.

(Synthesis Example 4) Synthesis of TeF-2

A container (internal capacity: 500 mL) equipped with a stirrer, a condenser tube, and a burette was prepared. In this container, 30 g (161 mmol) of 4,4-biphenol (reagent manufactured by Tokyo Kasei Kogyo Co., Ltd.), 5.4 g (40 mmol) of terephthalaldehyde (reagent manufactured by Tokyo Kasei Kogyo Co., Ltd.), and 300 g of Ethylglyme (special grade reagent manufactured by Tokyo Kasei Kogyo Co., Ltd.) were charged, and 3.9 g (21 mmol) of p-toluenesulfonic acid (reagent manufactured by Kanto Chemical Co., Inc.) was added thereto to prepare a reaction solution. This reaction solution was stirred at 90° C. for 3 hours to perform reaction. Next, the reaction solution was concentrated. The reaction product was precipitated by the addition of 50 g of heptane. After cooling to room temperature, the precipitates were separated by filtration. The solid matter obtained by filtration was dried, and then separated and purified by column chromatography to obtain 3.2 g of the objective compound (TeF-2) represented by the following formula.

The following peaks were found by 400 MHz-$^1$H-NMR, and the compound was confirmed to have a chemical structure of the following formula.

$^1$H-NMR: (d-DMSO, internal standard TMS)
δ (ppm) 9.4 (8H, O—H), 6.8 to 7.8 (32H, Ph-H), 6.2 (2H, C—H)

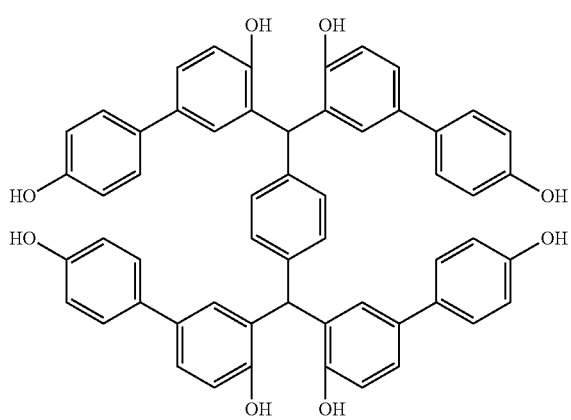

(TeF-2)

As a result of organic elemental analysis, the obtained compound (TeF-2) had a carbon concentration of 79.79% and an oxygen concentration of 15.18%. Because of the high carbon content and the low oxygen content, the compound (TeF-2) was evaluated as having high etching resistance.

As a result of measuring the molecular weight of the obtained compound by the above method, the molecular weight was determined to be 842.

As a result of thermogravimetry (TG), the 10% thermal reduction temperature of the obtained compound (TeF-2) was determined to be 400° C. or higher. Therefore, this compound was evaluated as having high heat resistance and being applicable to baking at a high temperature.

As a result of evaluating solubility in PGME and PGMEA, it was determined to be 30 wt % or more (evaluation A), and the compound (TeF-2) was evaluated as having excellent solubility. Therefore, the compound (TeF-2) was evaluated as having high storage stability in a solution state and being sufficiently applicable to even an edge bead rinse liquid (PGME/PGMEA mixed solution) widely used in the finer processing of semiconductors.

(Synthesis Example 5) Synthesis of TetP-1

In a four necked flask (1000 mL) sufficiently dried, substituted with nitrogen, and equipped with a dropping funnel, a Dimroth condenser tube, a thermometer, and a stirring blade, 108.8 g/0.8 mol of 2,3,6-trimethylphenol manufactured by Honshu Chemical Industry Co., Ltd. and 18.4 g/0.1 mol of 2,7-naphthalenedicarboxaldehyde manufactured by Mitsubishi Gas Chemical Company, Inc. were mixed under a nitrogen gas stream, and dissolved by heating to about 60° C. Then, 0.1 mL of sulfuric acid, 0.8 mL of 3-mercaptopropionic acid, and 10 mL of toluene were added, and the mixture was reacted while stirring.

After the reaction terminated, it was stood to cool, and after it reached room temperature, it was cooled in an ice bath. It was left at rest for 1 hour, to produce a target light yellow crude crystal, which was filtered. Subsequently, the crude crystal was washed with warm water of 60° C. by stirring and recrystallized to obtain 8.99 g of the product represented by the following formula (TetP-1).

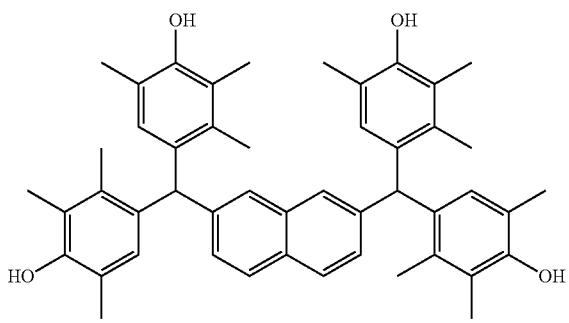

(TetP-1)

(Synthesis Example 6) Synthesis of CR-1

74.3 g (3.71 mol) of anhydrous HF and 50.5 g (0.744 mol) of $BF_3$ were charged into a temperature-controllable autoclave (made of SUS316L) having an internal capacity of 500 mL and equipped with an electromagnetic stirring device, and the content was stirred and increased in pressure with carbon monoxide to 2 MPa while maintaining the liquid temperature to −30° C. Thereafter, while maintaining the pressure to 2 MPa and the liquid temperature to −30° C., a raw material obtained by mixing 57.0 g (0.248 mol) of 4-cyclohexylbenzene and 50.0 g of n-heptane was fed thereto. After maintaining the content for 1 hour, the content was collected into ice, diluted with benzene, and neutralized to provide an oily layer, which was analyzed by gas chromatograph for evaluating the reaction performance. The 4-cyclohexylbenzene conversion was 100%, and the 4-cyclohexylbenzaldehyde selectivity was 97.3%.

The target component was isolated by simple distillation and analyzed by GC-MS. That is, it was measured using Agilent 5975/6890N manufactured by Agilent Corporation. The result exhibited a molecular weight of 188, which was 4-cyclohexylbenzaldehyde (CHBAL) as the following formula. The chemical shift value of $^1$H-NMR in a deuterated chloroform solvent (δ ppm, TMS standard) was 1.0 to 1.6 (m, 10H), 2.6 (m, 1H), 7.4 (d, 2H), 7.8 (d, 2H), and 10.0 (s, 1H).

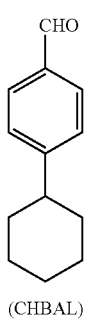

(CHBAL)

Under a nitrogen gas stream, resorcinol manufactured by Kanto Chemical Co., Inc. (22 g, 0.2 mol), the above 4-cyclohexylbenzaldehyde (46.0 g, 0.2 mol), and dehydrated ethanol (200 mL) were charged to a four necked flask (1000 mL) sufficiently dried, substituted with nitrogen, and equipped with a dropping funnel, a Dimroth condenser tube, a thermometer, and a stirring blade, to prepare an ethanol solution. This solution was heated to 85° C. by a mantle heater while stirring. Then, 75 mL of concentrated hydrochloric acid (35%) was dropped through the dropping funnel for 30 minutes, and continuously stirred at 85° C. for 3 hours. After the reaction terminated, it was stood to cool, and after it reached room temperature, it was cooled in an ice bath. It was left at rest for 1 hour, to produce a target light yellow crude crystal, which was filtered. The crude crystal was washed twice with 500 mL of methanol, filtered, and dried in a vacuum to obtain 50 g of the product represented by the following formula (CR-1).

As a result of LC-MS analysis for the product, the molecular weight was determined to be 1121. The chemical shift value (δ ppm, TMS standard) of $^1$H-NMR of the product in a deuterated chloroform solvent was 0.8 to 1.9 (m, 44H), 5.5, 5.6 (d, 4H), 6.0 to 6.8 (m, 24H), and 8.4, 8.5 (m, 8H). From these results, the obtained product was identified as an objective compound (CR-1) (yield: 91%).

(CR-1)

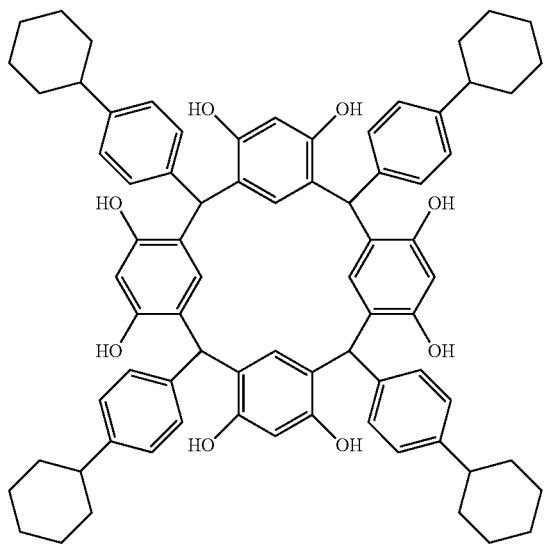

Examples 1 to 2 and Comparative Examples 1 and 2

The following tests were conducted as Example 1 using the compound obtained in Synthesis Example 1, Example 2 using the compound obtained in Synthesis Example 2, Example 3 using the compound obtained in Synthesis Example 3, Example 4 using the compound obtained in Synthesis Example 4, Comparative Example 1 using the compound obtained in Synthesis Example 5, and Comparative Example 2 using the compound obtained in Synthesis Example 6.

(2) Resist Performance Test

Each component was blended according to Table 1 to prepare a homogeneous solution. The homogenous solution was then filtered through a Teflon membrane filter having a pore diameter of 0.1 μm to prepare a resist composition.

Of the above components, as the acid generating agent (C), the acid crosslinking agent (G), the acid diffusion controlling agent (E), and the solvent, the followings were used:

Acid Generating Agent (C)
P-1: triphenylbenzenesulfonium trifluoromethanesulfonate (Midori Kagaku Co., Ltd.)
Acid Crosslinking Agent (G)
C-1: NIKALAC MW-100LM (Sanwa Chemical Co., Ltd.)
Acid Diffusion Controlling Agent (E)
Q-1: trioctylamine (Tokyo Kasei Kogyo Co., Ltd.)
Solvent
S-1: propylene glycol monomethyl ether (Tokyo Kasei Kogyo Co., Ltd.)

Each prepared resist composition was evaluated for its heat resistance by the following procedures. A clean silicon wafer was spin coated with a resist, and then baked in an oven of 110° C. to form a resist film with a thickness of 60 nm. The film was visually observed.

As a result, all of the films were confirmed to be good films having no defect and have good heat resistance (evaluation: ○ (good)).

Then, each resist composition was evaluated for patterning by the following procedures.

A clean silicon wafer was spin coated with a resist, and then prebaked (PB) before exposure in an oven of 110° C. to form a resist film having a thickness of 60 nm. The resist film was irradiated with electron beams of 1:1 line and space setting with a 50 nm interval, a 40 nm interval, and a 25 nm interval using an electron beam lithography system (ELS-7500 manufactured by ELIONIX INC.). After irradiation, it was heated at each predetermined temperature for 90 seconds, and immersed in 2.38% by weight TMAH alkaline developing solution for 60 seconds for development. Subsequently, it was washed with ultrapure water for 30 seconds, and dried to form a negative type resist pattern.

The obtained line and space were observed by a scanning electron microscope (S-4800 manufactured by Hitachi High-Technologies Corporation).

The pattern having the resolution of 25 nm was evaluated for whether or not pattern shape, line edge roughness, and sensitivity were good. That is, a resist pattern having good pattern shape, line edge roughness, and sensitivity was evaluated as ○ (good). Failure in formation of a resist pattern was evaluated as x (poor). The evaluation results are shown in Table 1.

The minimum line width of the pattern which could be well formed was used as the resolution of the pattern. The rectangular pattern shape was evaluated as having good pattern shape. As for the line edge roughness, a pattern having asperities of less than 5 nm was evaluated as having good line edge roughness. The dose amount (μC/cm$^2$) in this case was used as sensitivity. The dose amount of less than 150 μC/cm$^2$ was evaluated as having good sensitivity.

As is evident from Table 1, resist patterns having good resolution of 25 nm and good sensitivity could be obtained by using the resists of Examples 1 to 4. The roughness of the patterns was also small, and their shapes were also good.

On the other hand, in the resists of Comparative Examples 1 and 2, resist patterns having good resolution of 40 nm could be obtained, but, a resist pattern having resolution of 25 nm could not be obtained.

TABLE 1

| | Solubility test of compound in safe solvent | | Compound of Synthesis Example | Acid generating agent (P-1) | Acid crosslinking agent (C-1) | Acid diffusion controlling agent (Q-1) | Solvent (S-1) | Heat resistance evaluation | Resist pattern evaluation |
|---|---|---|---|---|---|---|---|---|---|
| | PGME | PGMEA | (g) | (g) | (g) | (g) | (g) | | |
| Example 1 (BiF-1) | A | A | 1 | 0.3 | 0.3 | 0.03 | 30 | ○ | ○ |
| Example 2 (BiF-2) | A | A | 1 | 0.3 | 0.3 | 0.03 | 30 | ○ | ○ |
| Example 3 (TeF-1) | A | A | 1 | 0.3 | 0.3 | 0.03 | 30 | ○ | ○ |
| Example 4 (TeF-2) | A | A | 1 | 0.3 | 0.3 | 0.03 | 30 | ○ | ○ |
| Comparative Example 1 (TetP-1) | B | B | 1 | 0.3 | 0.3 | 0.03 | 30 | ○ | X |
| Comparative Example 2 (CR-1) | B | C | 1 | 0.3 | 0.3 | 0.03 | 30 | ○ | X |

As seen in the above results, the resist composition containing the compound (BiF-1), (BiF-2), (TeF-1), or (TeF-2) used in the present embodiment has higher sensitivity than that of the composition containing the compound (TetP-1) or (CR-1), and enables the formation of the resist pattern having a better shape having smaller roughness. As long as the above configuration of the present embodiment is satisfied, compounds other than those described in examples also exhibit the same effects.

This application claims a priority based on Japanese Patent Application No. 2014-050767 filed on Mar. 13, 2014, the entire contents of which are hereby incorporated by reference.

The present invention is suitably used in a resist composition which contains a compound represented by a specific chemical structural formula and is useful as a resist material, and a method for forming a resist pattern using the resist composition.

The invention claimed is:

1. A resist composition comprising a compound represented by the following formula (1):

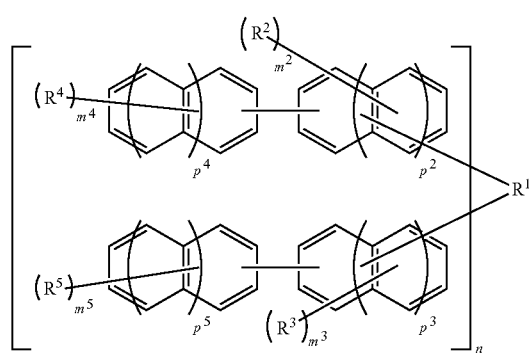

(1)

wherein $R^1$ is a group represented by $R^A$-$R^B$, wherein $R^A$ is a methine group, and $R^B$ is an aryl group having 7 or more carbon atoms; $R^2$ to $R^5$ are each independently a linear, branched or cyclic alkyl group having 1 to 10 carbon atoms, an aryl group having 6 to 10 carbon atoms, an alkenyl group having 2 to 10 carbon atoms, a thiol group, or a hydroxyl group, wherein at least one of $R^4$ and/or at least one of $R^5$ is a hydroxyl group and/or a thiol group; $m^2$ and $m^3$ are each independently an integer of 0 to 8; $m^4$ and $m^5$ are each independently an integer of 0 to 9, wherein at least one of $m^4$ and $m^5$ is an integer of 1 to 9; n is 1; and $p^2$ to $p^5$ are each independently an integer of 0 to 2; and at least one of an acid generating agent and an acid crosslinking agent, wherein at least one of $R^2$ and/or at least one of $R^3$ is a hydroxyl group and/or a thiol group.

2. The resist composition according to claim 1, wherein the compound represented by the formula (1) is a compound represented by the following formula (1a):

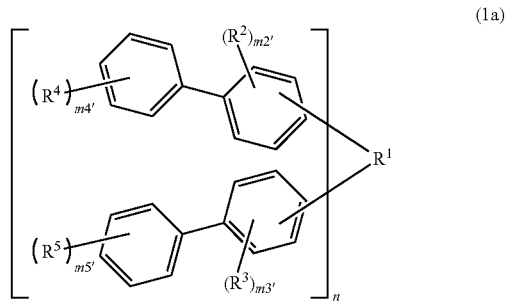

(1a)

wherein $R^1$ to $R^5$ and n are the same as defined in the formula (1); $m^{2'}$ and $m^{3'}$ are each independently an integer of 0 to 4; and $m^{4'}$ and $m^{5'}$ are each independently an integer of 0 to 5, wherein at least one of $m^{4'}$ and $m^{5'}$ is an integer of 1 to 5.

3. The resist composition according to claim 2, wherein the compound represented by the formula (1a) is a compound represented by the following formula (1b):

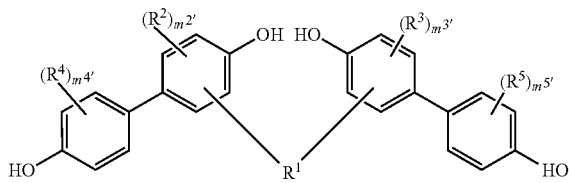

wherein $R^1$ is the same as defined in the formula (1); $m^{2'}$ and $m^{3'}$ are each independently an integer of 0 to 3; and $m^{4'}$ and $m^{5'}$ are each independently an integer of 0 to 5.

4. The resist composition according to claim 3, wherein the compound represented by the formula (1b) is a compound represented by the following formula (BiF-1):

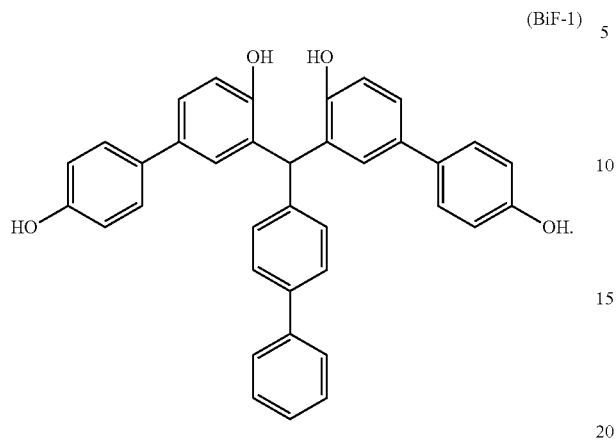

5. The resist composition according to claim 1, further comprising a solvent.

6. The resist composition according to claim 1, further comprising an acid generating agent.

7. The resist composition according to claim 1, further comprising an acid crosslinking agent.

8. A method for forming a resist pattern, comprising the steps of:
   coating a substrate with the resist composition according to claim 6, thereby forming a resist film;
   exposing the formed resist film; and
   developing the exposed resist film.

* * * * *

UNITED STATES PATENT AND TRADEMARK OFFICE
CERTIFICATE OF CORRECTION

| | |
|---|---|
| PATENT NO. | : 10,303,055 B2 |
| APPLICATION NO. | : 15/125463 |
| DATED | : May 28, 2019 |
| INVENTOR(S) | : Takashi Sato and Masatoshi Echigo |

Page 1 of 1

It is certified that error appears in the above-identified patent and that said Letters Patent is hereby corrected as shown below:

In the Claims

Column 70, Line (57-64):

In Claim 3, delete " 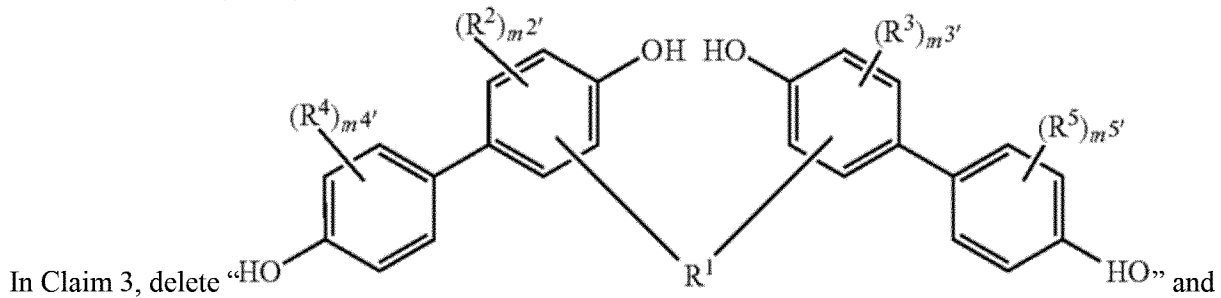 " and insert -- 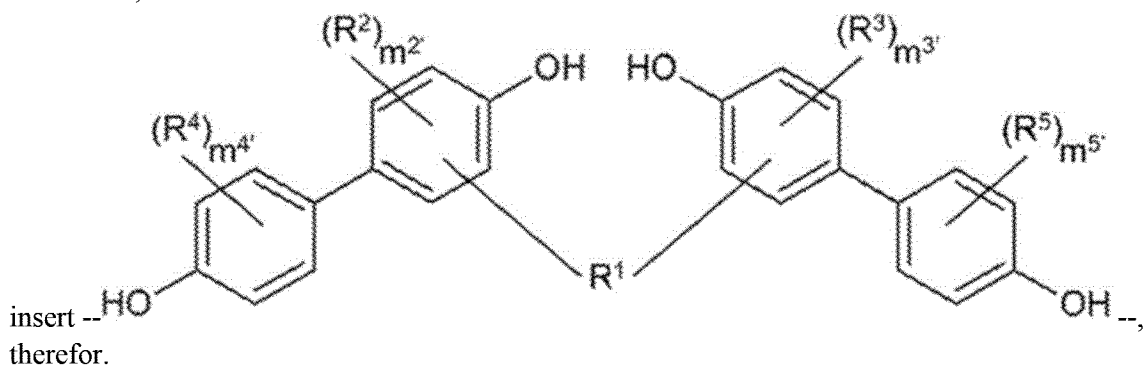 --, therefor.

Signed and Sealed this
Seventeenth Day of September, 2019

Andrei Iancu
*Director of the United States Patent and Trademark Office*